(12) United States Patent
Song et al.

(10) Patent No.: US 7,431,922 B2
(45) Date of Patent: Oct. 7, 2008

(54) BIOADHESIVE DIRECTED SOMATIC CELL THERAPY

(75) Inventors: Sun Uk Song, Inchon (KR); Youngsuk Yi, Gaithersburg, MD (US); Kwan Hee Lee, Gaithersburg, MD (US)

(73) Assignee: TissueGene, Inc., Rockville, MD (US)

( * ) Notice: Subject to any disclaimer, the term of this patent is extended or adjusted under 35 U.S.C. 154(b) by 359 days.

(21) Appl. No.: 10/382,190

(22) Filed: Mar. 5, 2003

(65) Prior Publication Data
US 2004/0018179 A1 Jan. 29, 2004

Related U.S. Application Data

(60) Provisional application No. 60/369,111, filed on Mar. 29, 2002.

(51) Int. Cl.
*A61K 48/00* (2006.01)
*A01N 63/00* (2006.01)

(52) U.S. Cl. .................. 424/93.21; 424/93.1; 424/93.2

(58) Field of Classification Search ....................... None
See application file for complete search history.

(56) References Cited

U.S. PATENT DOCUMENTS

| | | | |
|---|---|---|---|
| 5,700,774 A | 12/1997 | Hattersley et al. | |
| 5,766,585 A | 6/1998 | Evans et al. | |
| 5,785,964 A * | 7/1998 | Naughton et al. | 424/93.21 |
| 5,842,477 A | 12/1998 | Naughton et al. | |
| 5,846,931 A | 12/1998 | Hattersley et al. | |
| 5,858,355 A | 1/1999 | Glorioso et al. | |
| 6,151,525 A | 11/2000 | Soykan et al. | |
| 6,291,240 B1 * | 9/2001 | Mansbridge et al. | 435/395 |
| 6,315,992 B1 | 11/2001 | Noh et al. | |
| 6,413,511 B1 * | 7/2002 | Glorioso et al. | 424/93.21 |
| 6,582,391 B2 * | 6/2003 | Mineau-Hanschke | 604/19 |
| 6,811,777 B2 * | 11/2004 | Mishra | 424/93.72 |
| 2003/0175250 A1 * | 9/2003 | Jager et al. | 424/93.7 |

OTHER PUBLICATIONS

Marx et al, Oral Srug, Oral Med, Oral Pathol, Oral Radiol and Endodontol 1998;85:638-46.*
Jensen et al, Intl Ortho 2005;29:67-72.*
Game et al, Wien Klin Wochenschr 2001;113:823-38.*
Platt et al, Nat Biotech Mar. 2002;20(3)231-2.*
Kaps et al, Arthritis Rheum Jan. 2002;46:149-62.*
Cheng et al, Calcif Tissue Int Feb. 2001;68:87-94.*
Gelse et al, Arthritis Rehmat 2001;44:1943-53.*
Doherty et al, J Rhematol 2000;27:1725-31.*
Lee et al., "Regeneration of Hyaline Cartilage by Cell-Mediated Gene Therapy Using Transforming Growth Factor Beta-1-Producing Fibroblasts", Human Gene Therapy (2001), 12: 1805-1813.
Mrowiec et al., "A Novel Technique for Preparing Improved Buffy Coat Platelet Concentrates", Blood Cells, Molecules, and Diseases (1995), 21(1): 25-33(9) (abstract only).
Viggeswarapu et al., Adenoviral delivery of LIM mineralization protein-1 induces new-bone formation in vitro and in vivo, Mar. 2001, 83(3): 364-376.

* cited by examiner

*Primary Examiner*—Q. Janice Li
(74) *Attorney, Agent, or Firm*—Joseph Hyosuk Kim; JHK Law

(57) ABSTRACT

The subject invention is related to a cell-mediated gene therapy treatment using a cell composition that includes bioadhesive material. The bioadhesive material allows targeted and localized delivery of therapeutic somatic cells to the site of interest.

27 Claims, 17 Drawing Sheets

Figure 6
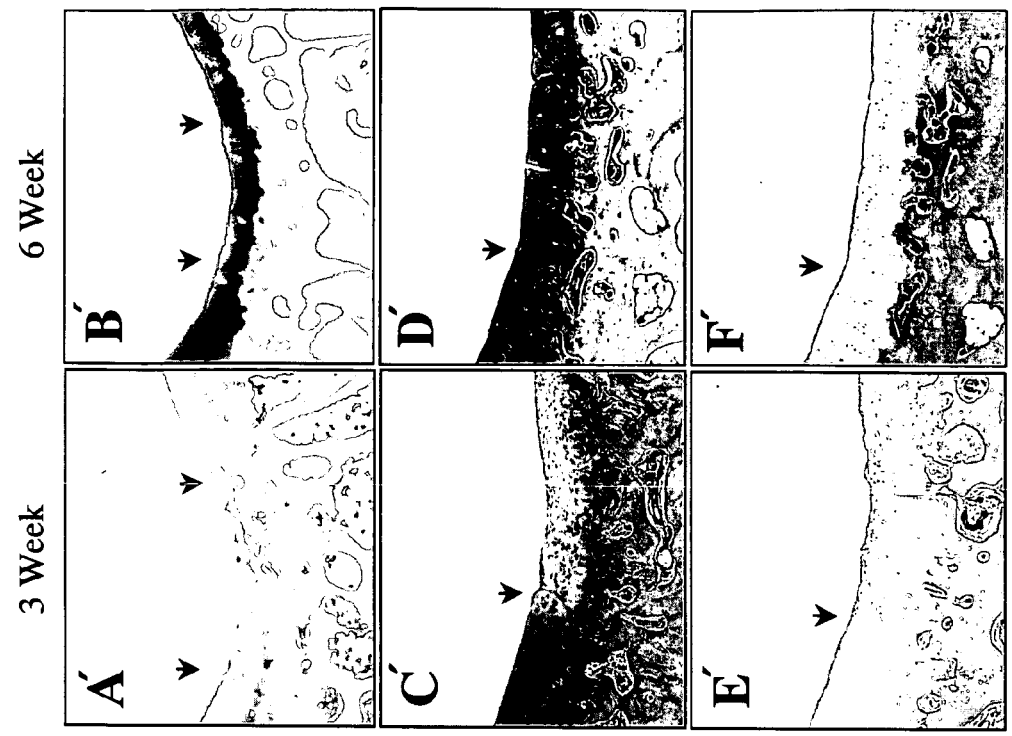
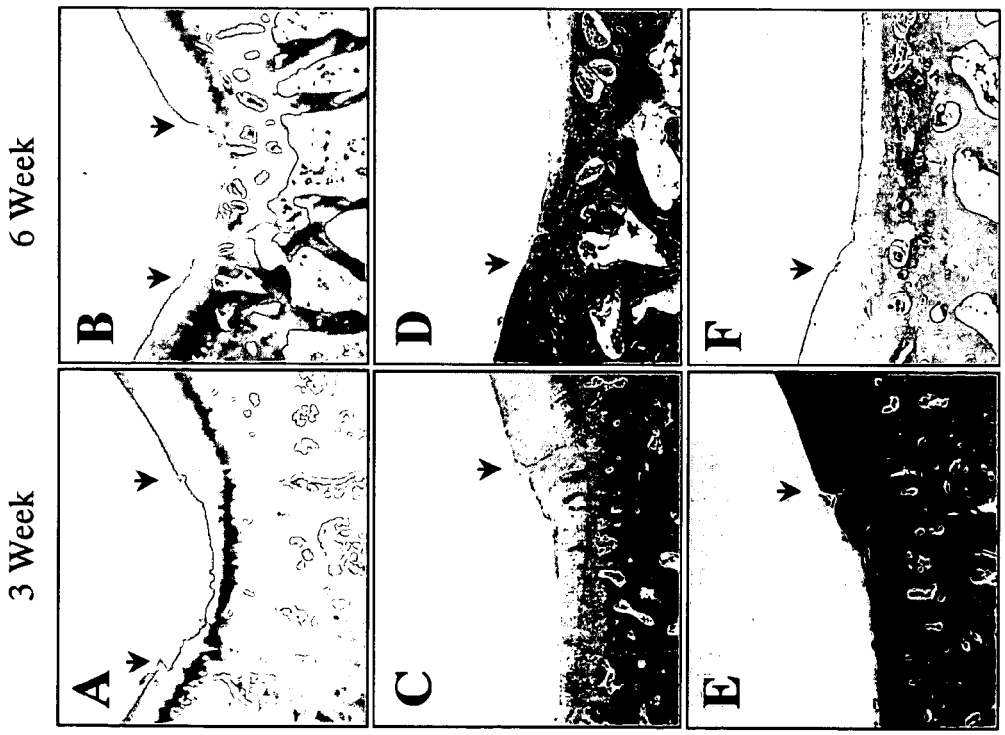

hChon+3T3-TGF β1
(6 wk)

Control
(6 wk)

hChon+3T3-TGF β1
(12 wk)

Control
(12 wk)

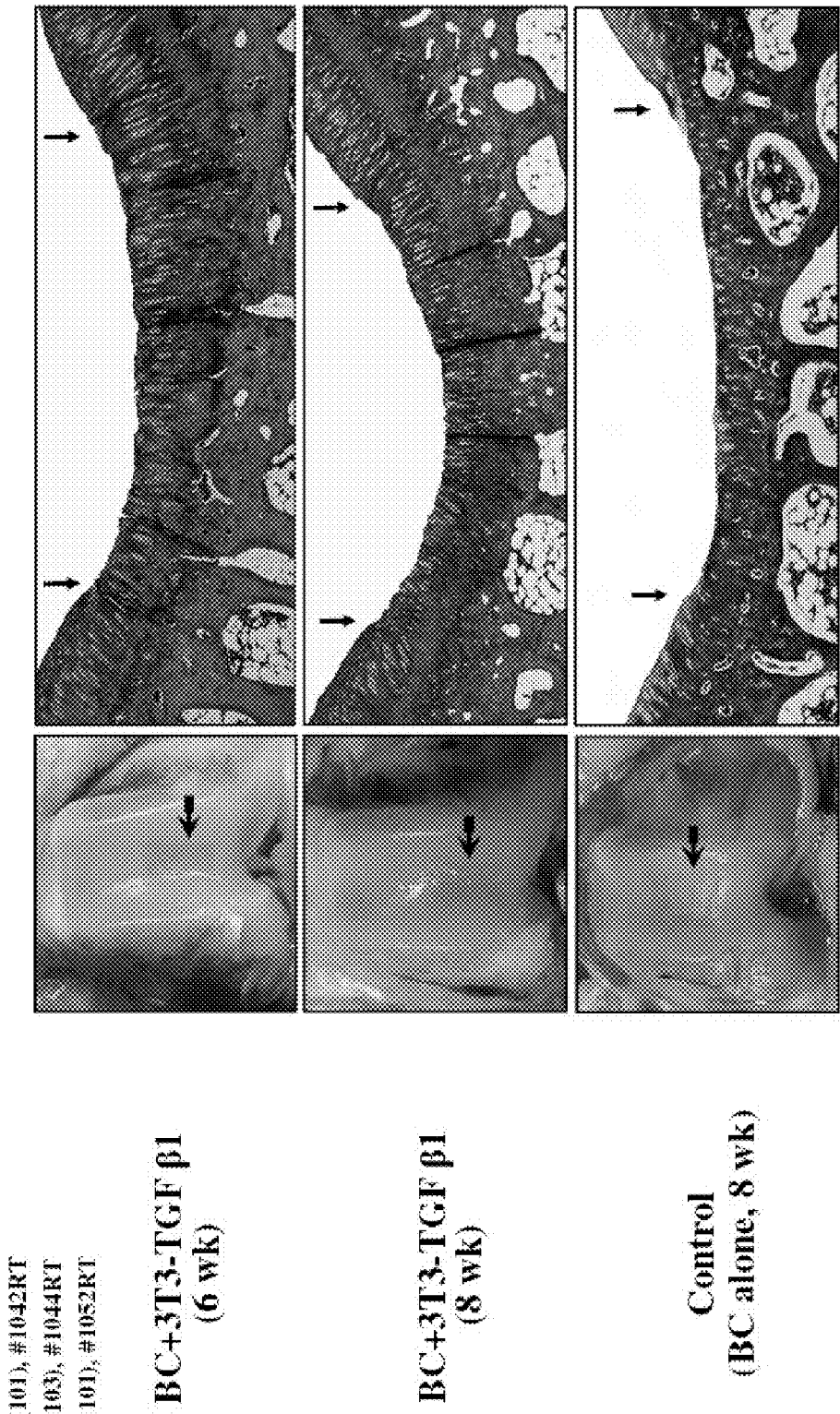
Fig. 16 Buffy Coat-Cell Injection (Rabbit, Partial Defect)

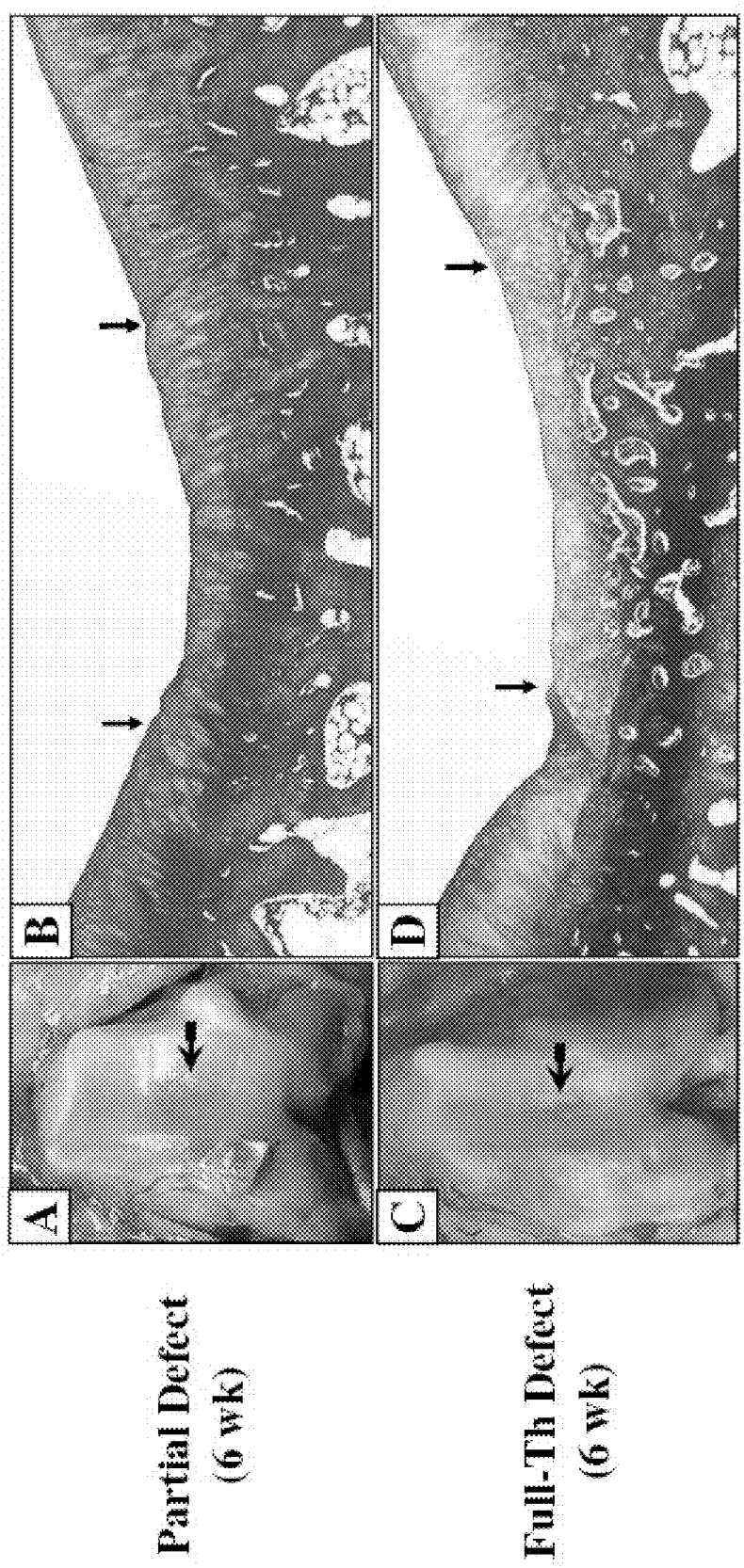
Fig 17. Cartilage regeneration by transplantation of mixture of hChon and hChon-TGFβ1 with Greenplast (GP)

BIOADHESIVE DIRECTED SOMATIC CELL THERAPY

The present application claims the benefit of priority to U.S. Provisional Application No. 60/369,111, filed Mar. 29, 2002, the contents of which are incorporated by reference herein in their entirety.

BACKGROUND OF THE INVENTION

1. Field of the Invention

The present invention relates to a bioadhesive directed gene therapy composition for localized expression of a gene of interest, including various cytokines. The present invention also relates to a method of using the composition to regenerate cartilage. In addition, the present invention relates to a method of treating osteoarthritis by injecting the composition to a mammalian connective tissue.

2. Brief Description of the Related Art

In the orthopedic field, degenerative arthritis or osteoarthritis is the most frequently encountered disease associated with cartilage damage. Almost every joint in the body, such as the knee, the hip, the shoulder, and even the wrist, is affected. The pathogenesis of this disease is the degeneration of hyaline articular cartilage (Mankin et al., J Bone Joint Surg, 52A: 460-466, 1982). The hyaline cartilage of the joint becomes deformed, fibrillated, and eventually excavated. If the degenerated cartilage could somehow be regenerated, most patients would be able to enjoy their lives without debilitating pain.

Traditional routes of drug delivery, such as oral, intravenous or intramuscular administration, to carry the drug to the joint are inefficient. The half-life of drugs injected intraarticularly is generally short. Another disadvantage of intraarticular injection of drugs is that frequent repeated injections are necessary to obtain acceptable drug levels at the joint spaces for treating a chronic condition such as arthritis. Because therapeutic agents heretofore could not be selectively targeted to joints, it was necessary to expose the mammalian host to systemically high concentrations of drugs in order to achieve a sustained, intra-articular therapeutic dose. Exposure of non-target organs in this manner exacerbated the tendency of anti-arthritis drugs to produce serious side effects, such as gastrointestinal upset and changes in the hematological, cardiovascular, hepatic and renal systems of the mammalian host.

In the orthopedic field, some cytokines have been considered as candidates for the treatment of orthopedic diseases. Bone morphogenetic protein has been considered to be an effective stimulator of bone formation (Ozkaynak et al., EMBO J, 9:2085-2093, 1990; Sampath and Rueger, Complications in Ortho, 101-107, 1994), and TGF-$\beta$ has been reported as a stimulator of osteogenesis and chondrogenesis (Joyce et al., J Cell Biology, 110:2195-2207, 1990).

Transforming growth factor-$\beta$ (TGF-$\beta$) is considered to be a multifunctional cytokine (Sporn and Roberts, Nature (London), 332: 217-219, 1988), and plays a regulatory role in cellular growth, differentiation and extracellular matrix protein synthesis (Madri et al., J Cell Biology, 106: 1375-1384, 1988). TGF-$\beta$ inhibits the growth of epithelial cells and osteoclast-like cells in vitro (Chenu et al., Proc Natl Acad Sci, 85: 5683-5687, 1988), but it stimulates enchondral ossification and eventually bone formation in vivo (Critchlow et al., Bone, 521-527, 1995; Lind et al., A Orthop Scand, 64(5): 553-556, 1993; and Matsumoto et al., In vivo, 8: 215-220, 1994). TGF-$\beta$-induced bone formation is mediated by its stimulation of the subperiosteal pluripotential cells, which eventually differentiate into cartilage-forming cells (Joyce et al., J Cell Biology, 110: 2195-2207, 1990; and Miettinen et al., J Cell Biology, 127-6: 2021-2036, 1994).

The biological effect of TGF-$\beta$ in orthopedics has been reported (Andrew et al., Calcif Tissue In. 52: 74-78, 1993; Borque et al., Int J Dev Biol., 37:573-579, 1993; Carrington et al., J Cell Biology, 107:1969-1975, 1988; Lind et al., A Orthop Scand. 64(5):553-556, 1993; Matsumoto et al., In vivo, 8:215-220, 1994). In mouse embryos, staining shows that TGF-$\beta$ is closely associated with tissues derived from the mesenchyme, such as connective tissue, cartilage and bone. In addition to embryologic findings, TGF-$\beta$ is present at the site of bone formation and cartilage formation. It can also enhance fracture healing in rabbit tibiae. Recently, the therapeutic value of TGF-$\beta$ has been reported (Critchlow et al., Bone, 521-527, 1995; and Lind et al., A Orthop Scand, 64(5): 553-556, 1993), but its short-term effects and high cost have limited wide clinical application.

Intraarticular injection of TGF-$\beta$ for the treatment of arthritis is not desirable, because the injected TGF-$\beta$ has a short duration of action, as TGF-$\beta$ is degraded into inactive form in vivo. Therefore, a new method for long-term release of TGF-$\beta$ is necessary for the regeneration of hyaline cartilage.

There have been reports of regeneration of articular cartilage with autotransplantation of cartilage cells (Brittberg et al., New Engl J Med 331: 889-895, 1994), but this procedure entails two operations with wide excision of soft tissues. If intraarticular injection is enough for the treatment of degenerative arthritis, it will be of great economic and physical benefit to the patients.

Gene therapy, which is a method of transferring a specific protein to a specific site, may be the answer to this problem (Wolff and Lederberg, Gene Therapeutics ed. Jon A. Wolff, 3-25, 1994; and Jenks, J Natl Cancer Inst, 89(16): 1182-1184, 1997).

U.S. Pat. Nos. 5,858,355 and 5,766,585 disclose making a viral or plasmid construct of the IRAP (interleukin-1 receptor antagonist protein) gene; transfecting synovial cells (U.S. Pat. No. 5,858,355) and bone marrow cells (U.S. Pat. No. 5,766,585) with the construct; and injecting the transfected cells into a rabbit joint, but there is no disclosure of using a gene belonging to the TGF-$\beta$ superfamily to regenerate connective tissue.

U.S. Pat. Nos. 5,846,931 and 5,700,774 disclose injecting a composition that includes a bone morphogenesis protein (BMP), which belongs to the TGF $\beta$ "superfamily", together with a truncated parathyroid hormone related peptide to effect the maintenance of cartilaginous tissue formation, and induction of cartilaginous tissue. However, there is no disclosure of a gene therapy method using the BMP gene.

U.S. Pat. No. 5,842,477 discloses implanting a combination of a scaffolding, periosteal/perichondrial tissue, and stromal cells, including chondrocytes, to a cartilage defected area. Since this patent disclosure requires that all three of these elements be present in the implanted system, the reference fails to disclose or suggest the simple gene therapy method of the invention which does not require the implantation of the scaffolding or the periosteal/perichondrial tissue.

U.S. Pat. No. 6,315,992 discloses that hyaline cartilage is generated in defected mammalian joint when fibroblast cells transfected with TGF-$\beta$1 are injected into the defected knee joint. However, the patent does not disclose the advantages of using a bioadhesive composition as in the present invention.

Lee et al., Human Gene Therapy, 12: 1085-1813, 2001 discloses that hyaline cartilage is generated in defected mammalian joint when fibroblast cells transfected with TGF-$\beta$1 are injected into the defected knee joint. However, Lee et al. does not disclose using a bioadhesive composition as in the present invention.

Mrowiec et al., Blood Cells, Molecules, and Diseases 21(3):25-33, 1995, shows a novel technique for preparing improved buffy coat platelet concentrates. However, Mrowiec et al. does not disclose mixing the purified buffy coat with cells for injection as a gene therapy composition.

In spite of these prior art disclosures, there remains a very real and substantial need for localized delivery of therapeutic gene products at the site in need thereof. In particular, there is a need to develop more effective and potent treatment method to regenerate connective tissue in the mammalian host.

SUMMARY OF THE INVENTION

The present invention has met the hereinbefore described need.

The present invention is directed to a composition comprising a treatment-effective amount of a population of mammalian somatic cells transfected or transduced with a therapeutic gene, and an adhesive-effective amount of bioadhesive material for administration into a mammalian site in need thereof. The bioadhesive material may be purified buffy coat. And the gene may encode a cytokine. Further, the cytokine may belong to TGF-β superfamily. Even further, cytokine may be, without limitation, TGF-β1, TGF-β2, TGF-β3, BMP-2, BMP-3, BMP-4, BMP-5, BMP-6, BMP-7, or BMP-9. Still further, the gene may encode TGF-β1 or BMP-2.

In the composition described above, the cell may be a connective tissue cell. And the connective tissue cell may be, without limitation, fibroblast or chondrocyte. Further, the fibroblast or chondrocyte cell may be transfected or transduced with any therapeutic gene, including a cytokine, such as the genes encoding a member of the TGF-β superfamily.

When purified buffy coat is used as the bioadhesive, the ratio of the amount of the buffy coat to cells may be from about 1-5 to 1 in terms of volume. In addition, the ratio may be about 1-3 to 1. And still further, the ratio may be from about 1 to 1.

In the composition above, the cells may be irradiated. And the cells may be mixed with cells that are not transfected or transduced with any DNA. The cells may be histocompatible with each other, in which case the cells may be derived from the same source organism. The cells may be also derived from different source organisms.

The present invention is also directed to a storage container for storing the above-described cells at a temperature of about −70° C. to about −196° C.

The present invention is also directed to a method of localizing gene expression at a target site in a mammal, comprising mixing an adhesive-effective amount of a bioadhesive material with therapeutic somatic cells to form a composition, and administering the composition to the site in need thereof. In this method, the bioadhesive material may be purified buffy coat. And in this method, the somatic cells may be transfected or transduced with a recombinant vector comprising a therapeutic gene. The therapeutic gene may be a cytokine, such as, but not limited to, the genes encoding a member of the TGF-β superfamily.

In the method described above, the target site may be the joint space, and the gene may encode TGF-β1, TGF-β2, TGF-β3, BMP-2, BMP-3, BMP-4, BMP-5, BMP-6, or BMP-7. In particular, the gene may encode TGF-β1 or BMP-2.

In the method described above, the cells may be irradiated. Also, in the method described above, the cells may be syngeneic or allogeneic with respect to the host recipient.

The present invention also encompasses the method above, and in particular, the somatic cells comprise a mixture of a first type of cells that are transfected or transduced with DNA encoding a therapeutic gene, and a second type of cells that are not transfected or transduced with DNA encoding a therapeutic gene. In the method, the cells may be stored prior to transplantation. And in particular, cells may be stored in a cryoperservative prior to transplantation. Furthermore, the transfection or transduction may be accomplished by liposome encapsulation, calcium phosphate coprecipitation, electroporation, DEAE-dextran mediation or viral mediation.

In another embodiment, the present invention is directed to a method of generating hyaline cartilage in a mammal comprising: a) generating a recombinant vector comprising a DNA sequence encoding transforming growth factor β (TGF-β) or bone morphogenetic protein (BMP) operatively linked to a promoter; b) transfecting or transducing a population of fibroblast or chondrocyte cells in vitro with said recombinant vector; and c) injecting an injectable mixed cell composition comprising hyaline cartilage-generating effective amount of (i) a population of fibroblast or chondrocyte cells transfected or transduced with a gene encoding TGF-β or BMP; (ii) an adhesive effective amount of bioadhesive material; and (iii) a pharmaceutically acceptable carrier thereof, into a joint space of a mammal such that expression of the DNA sequence encoding TGF-β or BMP within the joint space occurs resulting in the generation of hyaline cartilage in the joint space.

In yet another embodiment of the invention, the invention is directed to a method of generating hyaline cartilage in a mammal comprising: a) generating a recombinant vector comprising a DNA sequence encoding transforming growth factor β (TGF-β) or bone morphogenetic protein (BMP) operatively linked to a promoter; b) transfecting or transducing a population of fibroblast or chondrocyte cells in vitro with said recombinant vector; and c) injecting an injectable mixed cell composition comprising hyaline cartilage-generating effective amount of (i) a population of fibroblast or chondrocyte cells transfected or transduced with a gene encoding TGF-β or BMP; (ii) a population of fibroblast or chondrocyte cells that have not been transfected or transduced with a gene encoding TGF-β or BMP; (iii) an adhesive effective amount of bioadhesive material; and (iv) a pharmaceutically acceptable carrier thereof, into a joint space of a mammal such that expression of the DNA sequence encoding TGF-β or BMP within the joint space occurs resulting in the generation of hyaline cartilage in the joint space.

In yet another embodiment of the invention, the invention is directed to a method of treating osteoarthritis comprising: a) generating a recombinant vector comprising a DNA sequence encoding transforming growth factor β (TGF-β) or bone morphogenetic protein (BMP) operatively linked to a promoter; b) transfecting/transducing a population of fibroblast or chondrocyte cells in vitro with said recombinant vector; and c) injecting an injectable mixed cell composition comprising bone- and hyaline-generating effective amount of (i) a population of fibroblast or chondrocyte cells transfected or transduced with a gene encoding TGF-β or BMP; (ii) an adhesive effective amount of bioadhesive material; and (iii) a pharmaceutically acceptable carrier thereof, into a joint space of a mammal such that expression of the DNA sequence encoding TGF-β or BMP within the joint space occurs resulting in the generation of bone and cartilage cartilage in the joint space.

In still another embodiment, the invention is directed to a method of treating osteoarthritis comprising: a) generating a recombinant vector comprising a DNA sequence encoding transforming growth factor β (TGF-β) or bone morphogenetic protein (BMP) operatively linked to a promoter; b) transfecting or transducing a population of fibroblast or chondrocyte cells in vitro with said recombinant vector; and c) injecting an injectable mixed cell composition comprising bone- and cartilage-generating effective amount of (i) a population of fibroblast or chondrocyte cells transfected or transduced with a gene encoding TGF-β or BMP; (ii) a population of fibroblast or chondrocyte cells that have not been transfected or transduced with a gene encoding TGF-β or BMP; (iii) an adhesive effective amount of bioadhesive material; and (iv) a pharmaceutically acceptable carrier thereof, into a joint space of a mammal such that expression of the DNA sequence encoding TGF-β or BMP within the joint space occurs resulting in the generation of bone and cartilage in the joint space.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein;

In FIG. 1A, total RNA was isolated from NIH 3T3 cells or NIH 3T3 cells stably transfected with pmTβ1, a TGF-β1 expression vector, which was grown in the absence or presence of zinc. Total RNA (15 mg) was probed with either the TGF-β1 cDNA or β actin cDNA as a control. FIGS. 1B and 1C show expression of BMP2 in NIH3T3-BMP2 cells. FIGS. 1B and 1C show control NIH3T3-methallothionein (B) and NIH3T3-BMP2 cells (C). Blue color in panel (C) shows expression of BMP2 protein.

FIG. 2A shows a rectangular partial cartilage defect was made on the femoral condyle and the knee joint was injected with NIH 3T3 cells without TGF-β1 transfection. The defect was not covered. FIG. 2B shows that at 6 weeks after injection of NIH 3T3-TGF-β1 cells, the defect was covered by newly formed tissue. The color of the regenerated tissue was almost identical to that of the surrounding cartilage.

FIGS. 3A and 3B show hematoxilin-eosine (H&E) analysis of defect area 4 and 6 weeks after injection with control cells. No tissue covered the initial defect area. FIGS. 3C and 3D show hematoxilin-eosine (H&E) analysis of defect area 4 and 6 weeks after injection of TGF-β1-transfected cells. At 4 weeks, partial defect area was covered by hyaline cartilage after injection of TGF-β1-transfected cells. At 4 weeks and 6 weeks after injection, the regenerated tissue became thicker and its height was almost identical to normal cartilage at 6 weeks. Histologically, the regenerated cartilage (arrow) was identical to the surrounding hyaline cartilage.

FIG. 4A shows hyaline cartilage in a rabbit joint injected with control cells.

FIG. 5A shows that in the partially damaged area, the regenerated hyaline cartilage is shown by H&E staining (black arrow). FIG. 5B shows that in the completely denuded cartilage area, the regenerated tissue (white arrow) was fibrous collagen.

FIGS. 6A-6F and 6A'-6F' show regeneration of cartilage with irradiated NIH3T3-TGF-β1 fibroblast cells.

FIGS. 11A and 11C show pictures of the femoral condyles 6 weeks post injection with either a mixture of hChon (human chondrocytes) and NIH3T3-TGF-β1 cells (A) or hChon alone (C). FIGS. 11B and 11D show Mason's trichrome staining of sections from the femoral condyle injected with either a mixture of hChon and NIH3T3-TGF-β1 cells (B) or hChon alone (D). Original magnification: [(B & D)×12.5].

FIGS. 12A and 12D show pictures of the femoral condyles 12 weeks post injection with either a mixture of hChon and NIH3T3-TGF-β1 cells (A) or hChon alone (D). FIGS. 12B and 12E show Mason's trichrome staining, and FIG. 12C shows Safranin-O staining of sections from the femoral condyle injected with either a mixture of hChon and NIH3T3-TGF-β1 cells (B & C) or hChon alone (E). Original magnification: (B, C & E)×12.5.

FIGS. 13A and 13C show pictures of the femoral condyles 6 weeks post injection with either a mixture of hChon and NIH3T3-BMP-2 cells (A) or hChon alone (C). FIGS. 13B and 13D show Mason's trichrome staining of sections from the femoral condyle injected with either a mixture of hChon and NIH3T3-BMP-2 cells (B) or hChon alone (D). Original magnification: (B & D)×12.5.

FIGS. 14A and 14D show pictures of the femoral condyles 12 weeks post injection with either a mixture of hChon and NIH3T3-BMP-2 cells (A) or hChon alone (D). FIGS. 14B and 14E show Mason's trichrome staining and FIG. 14C shows Safranin-O staining of sections from the femoral condyle injected with either mixture of hChon and NIH3T3-BMP-2 cells (B & C) or hChon alone (E). Original magnification: (B, C & E)×12.5.

FIGS. 15A and 15C show pictures of the femoral condyles 6 weeks post injection with either a mixture of hChon and hChon-TGF-β1 cells (A) or hChon alone (C). FIGS. 15B and 15D show Mason's trichrome staining of sections from the femoral condyle injected with either mixture of hChon and hChon-TGF-β1 cells (B) or hChon alone (D). [Original magnification: (B & D)×12.5].

FIGS. 16A-16F show regeneration of cartilage with injection of a mixture of human buffy coat and NIH3T3-TGF-β1 cells in a rabbit knee joint with a partial defect.

FIGS. 17A-17D show pictures of the femoral condyles 6 weeks post injection with a mixture of hChon and hChon-TGF-β1 cells at either a partial (A) or full-thickness defect (C). FIGS. 17B and 17D show Mason's trichrome staining of sections from the femoral condyle injected with a mixture of hChon and hChon-TGF-β1 cells at a partial (B) or full-thickness defect (D). [Original magnification: (B& D)×12.5].

DETAILED DESCRIPTION OF THE INVENTION

Figure 1:
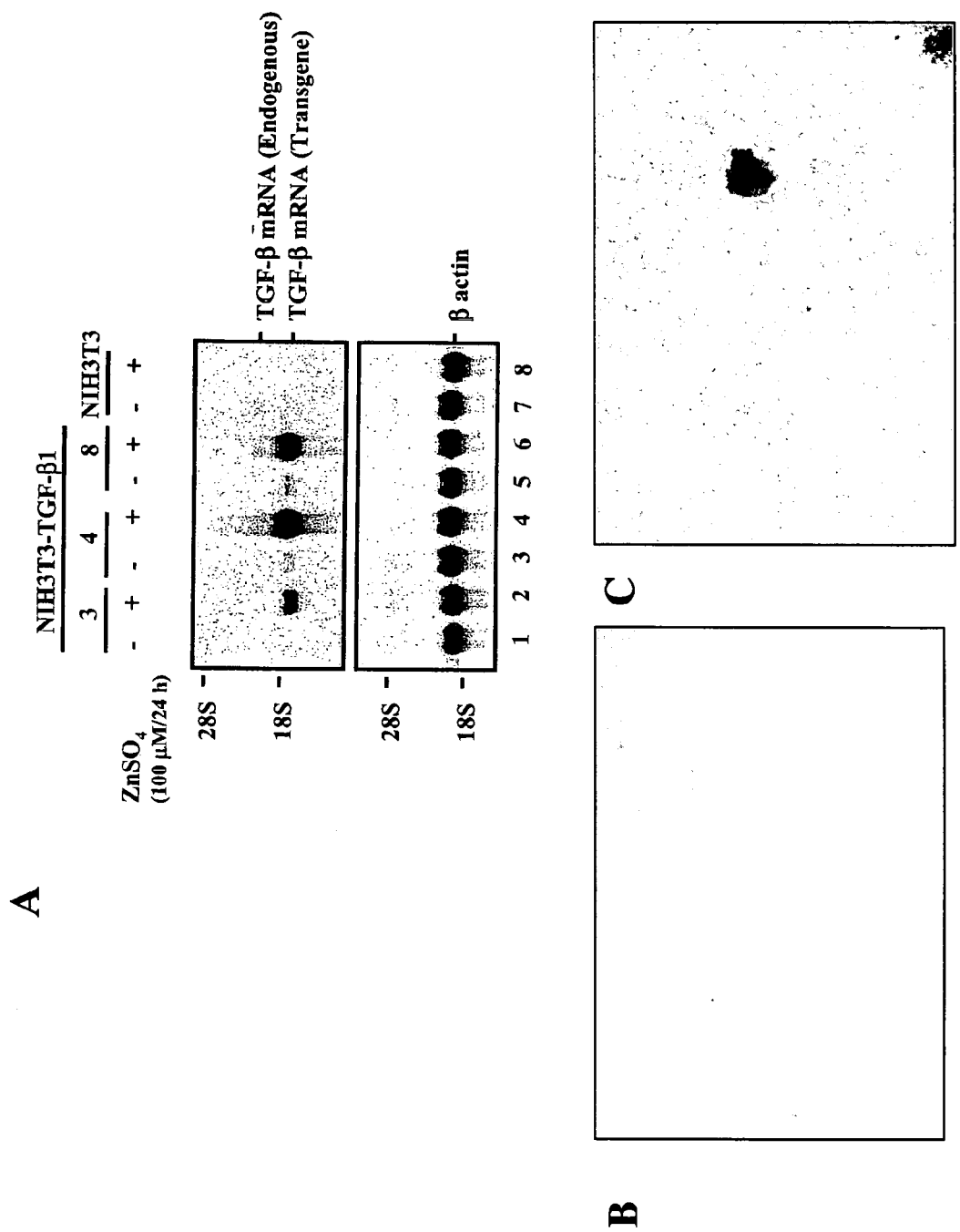
FIGS. 1A-1C show expression of TGF-β1 mRNA (A) and BMP2 (B and C).

As used herein, "bioadhesive" or "bio-adhesive" composition, formulation, material and so on refer to a naturally occurring or synthetic compound that adheres, binds or interacts with a biological tissue, including, but not limited to, connective tissue, and in particular, bone and cartilage. The bioadhesive used with the invention results in prolonging the residence time of the therapeutic somatic cell at the site of contact. Typically, the bioadhesive material is mixed with the somatic cells to produce an adhesive effective mixture.

As used herein, "biologically derived carrier molecule" refers to molecules that are naturally found in a mammal, which is useful as a carrier. Examples of it include albumin, glycosaminoglycans, heparin, hyaluronic acid, collagens, buffy coat and the like. The somatic cells may be mixed with these carrier molecules.

As used herein, the term "buffy coat" or "buffy crust" refers to a thin yellowish layer that contains leukocytes and platelets overlying the packed red cells in centrifuged blood.

As used herein, the term "connective tissue" is any tissue that connects and supports other tissues or organs, and includes but is not limited to a ligament, a cartilage, a tendon, a bone, and a synovium of a mammalian host.

As used herein, the terms "connective tissue cell" and "cell of a connective tissue" include cells that are found in the connective tissue, such as fibroblasts, cartilage cells (chondrocytes), and bone cells (osteoblasts/osteocytes), which secrete collagenous extracellular matrix, as well as fat cells (adipocytes) and smooth muscle cells. Preferably, the connective tissue cells are fibroblasts, cartilage cells, and bone cells. It will be recognized that the invention can be practiced with a mixed culture of connective tissue cells, as well as cells of a single type. It is also recognized that the tissue cells may be pretreated with chemical compounds or radiation before injecting them into the joint space so that the cells stably express the gene of interest within the host organism. Preferably, the connective tissue cell does not cause a negative immune response when injected into the host organism. It is understood that allogeneic cells may be used in this regard, as well as autologous cells for cell-mediated gene therapy or somatic cell therapy.

As used herein, "connective tissue cell line" includes a plurality of connective tissue cells originating from a common parent cell.

As used herein, "helper cells" refer to somatic cells that are not transfected or transduced with the therapeutic gene. In one embodiment, these cells are not transfected or transduced with any therapeutic gene. Helper cells are mixed with therapeutic somatic cells that produce the therapeutic gene product. Such helper cells may include any cell at all, including connective tissue cells, such as fibroblasts and chondrocytes.

As used herein, "hyaline cartilage" refers to the connective tissue covering the joint surface. By way of example only, hyaline cartilage includes, but is not limited to, articular cartilage, costal cartilage, and nose cartilage.

In particular, hyaline cartilage is known to be self-renewing, responds to alterations, and provides stable movement with less friction. Hyaline cartilage found even within the same joint or among joints varies in thickness, cell density, matrix composition and mechanical properties, yet retains the same general structure and function. Some of the functions of hyaline cartilage include surprising stiffness to compression, resilience, and exceptional ability to distribute weight loads, ability to minimize peak stress on subchondral bone, and great durability.

Grossly and histologically, hyaline cartilage appears as a slick, firm surface that resists deformation. The extracellular matrix of the cartilage comprises chondrocytes, but lacks blood vessels, lymphatic vessels or nerves. An elaborate, highly ordered structure that maintains interaction between chondrocytes and the matrix serves to maintain the structure and function of the hyaline cartilage, while maintaining a low level of metabolic activity. The reference O'Driscoll, J. Bone Joint Surg., 80A: 1795-1812, 1998 describes the structure and function of hyaline cartilage in detail, which is incorporated herein by reference in its entirety.

As used herein, "injectable" composition refers to a composition that excludes various three-dimensional scaffold, framework, mesh or felt structure may be made of any material or shape that allows cells to attach to it and allows cells to grow in more than one layer, and which structure is generally implanted, not injected. The injection is typically carried out by a syringe. However, any mode of injecting the composition of interest may be used. For instance, catheters, sprayers, or temperature dependent polymer gels also may be used.

As used herein, the term "mammalian host" includes members of the animal kingdom including but not limited to human beings.

As used herein, "mixed cell" or a "mixture of cells" or "cell mixture" refers to a combination of a plurality of different cell types. Preferably, the cells are used in cell-mediated gene therapy. More preferably, the cells are connective tissue cell that include cells that have been transfected or transduced with a gene or DNA encoding any therapeutic gene product. In particular, this gene product is a member of the transforming growth factor β superfamily. In addition, the mixture includes helper cells that have not been transfected or transduced with the therapeutic gene.

Using the transforming growth factor β superfamily of genes as an example of the type of therapeutic gene that may be used in the practice of the invention, and not by way of limiting the invention to any particular gene, typically, the ratio of cells that have not been transfected or transduced with a gene encoding a member of the transforming growth factor β superfamily to cells that have been transfected or transduced with a TGF superfamily gene may be in the range of about 3-20 to 1. The range may include about 3-10 to 1. In particular, the range may be about 10 to about 1 in terms of the number of cells. However, it is understood that the ratio of these cells should not be necessarily fixed to a particular range so long as the combination of these cells is effective to produce hyaline cartilage in partially and fully defected joints.

As used herein, the term "patient" includes members of the animal kingdom including but not limited to human beings.

As used herein, "pharmaceutically accepted carrier" refers to any carrier that is known in the art to promote the efficiency of transport of the composition of the invention and prolong the effectiveness of the composition.

As used herein, "somatic cell" or "cell" in general refers to the cell of the body other than egg or sperm.

As used herein, "stored" cells refer to a composition of mixed cells that have been either stored individually or together before they are administered to a mammalian host. The cells may be stored in a refrigeration unit. Or, the cells may be frozen at about −20° to −70° C. so that the cells are preserved for later administration into the mammalian host. The cells may be thawed using known protocols. The duration of freezing and thawing may be carried out by any number of ways, so long as the viability and potency of the cells are optimized.

As used herein, the "transforming growth factor-β (TGF-β) superfamily" encompasses a group of structurally related proteins, which affect a wide range of differentiation processes during embryonic development. The family includes, Müllerian inhibiting substance (MIS), which is required for normal male sex development (Behringer, et al., Nature, 345:167, 1990), *Drosophila decapentaplegic* (DPP) gene product, which is required for dorsal-ventral axis formation and morphogenesis of the imaginal disks (Padgett, et al., Nature, 325:81-84, 1987), the Xenopus Vg-1 gene product, which localizes to the vegetal pole of eggs (Weeks, et al., Cell, 51:861-867, 1987), the activins (Mason, et al., Biochem, Biophys. Res. Commun., 135:957-964, 1986), which can induce the formation of mesoderm and anterior structures in Xenopus embryos (Thomsen, et al., Cell, 63:485, 1990), and the bone morphogenetic proteins (BMP's, such as BMP-2, 3, 4, 5, 6 and 7, osteogenin, OP-1) which can induce de novo cartilage and bone formation (Sampath, et al., J. Biol. Chem., 265:13198, 1990). The TGF-β gene products can influence a variety of differentiation processes, including adipogenesis, myogenesis, chondrogenesis, hematopoiesis, and epithelial cell differentiation. For a review, see Massague, Cell 49:437, 1987, which is incorporated herein by reference in its entirety.

The proteins of the TGF-β family are initially synthesized as a large precursor protein, which subsequently undergoes proteolytic cleavage at a cluster of basic residues approximately 110-140 amino acids from the C-terminus. The C-terminal regions of the proteins are all structurally related and the different family members can be classified into distinct subgroups based on the extent of their homology. Although the homologies within particular subgroups range from 70% to 90% amino acid sequence identity, the homologies between subgroups are significantly lower, generally ranging from only 20% to 50%. In each case, the active species appears to be a disulfide-linked dimer of C-terminal fragments. For most of the family members that have been studied, the homodimeric species has been found to be biologically active, but for other family members, like the inhibins (Ung, et al., Nature, 321:779, 1986) and the TGF-β's (Cheifetz, et al., Cell, 48:409, 1987), heterodimers have also been detected, and these appear to have different biological properties than the respective homodimers.

Members of the superfamily of TGF-β genes include TGF-β3, TGF-β2, TGF-β4 (chicken), TGF-β1, TGF-β5 (Xenopus), BMP-2, BMP-4, Drosophila DPP, BMP-5, BMP-6, Vgr1, OP-1/BMP-7, Drosophila 60A, GDF-1, Xenopus Vgf, BMP-3, Inhibin-βA, Inhibin-βB, Inhibin-α, and MIS. These genes are discussed in Massague, Ann. Rev. Biochem. 67:753-791, 1998, which is incorporated herein by reference in its entirety.

Preferably, the member of the superfamily of TGF-β genes is TGF-β and BMP. More preferably, the member is TGF-β1, TGF-β2, TGF-β3, BMP-2, BMP-3, BMP-4, BMP-5, BMP-6, or BMP-7. Most preferably, the member is human or porcine TGF-β1 or BMP-2.

As used herein, "selectable marker" includes a gene product that is expressed by a cell that stably maintains the introduced DNA, and causes the cell to express an altered phenotype such as morphological transformation, or an enzymatic activity. Isolation of cells that express a transfected gene is achieved by optional introduction into the same cells a second gene that encodes a selectable marker, such as one having an enzymatic activity that confers resistance to an antibiotic or other drug. Examples of selectable markers include, but are not limited to, thymidine kinase, dihydrofolate reductase, aminoglycoside phosphotransferase, which confers resistance to aminoglycoside antibiotics such as kanamycin, neomycin and geneticin, hygromycin B phosphotransferase, xanthine-guanine phosphoribosyl transferase, CAD (a single protein that possesses the first three enzymatic activities of de novo uridine biosynthesis—carbamyl phosphate synthetase, aspartate transcarbamylase and dihydroorotase), adenosine deaminase, and asparagine synthetase (Sambrook et al. Molecular Cloning, Chapter 16, 1989), incorporated herein by reference in its entirety. It is understood that using a selectable marker is not a requirement to practice the claimed invention. In fact, in one embodiment, a selectable marker is not incorporated into the genetic construct of the claimed invention.

As used herein, a "promoter" can be any sequence of DNA that is active, and controls transcription in an eucaryotic cell. The promoter may be active in either or both eucaryotic and procaryotic cells. Preferably, the promoter is active in mammalian cells. The promoter may be constitutively expressed or inducible. Preferably, the promoter is inducible. Preferably, the promoter is inducible by an external stimulus. More preferably, the promoter is inducible by hormones or metals. Still more preferably, the promoter is inducible by heavy metals. Most preferably, the promoter is a metallothionein gene promoter. Likewise, "enhancer elements", which also control transcription, can be inserted into the DNA vector construct, and used with the construct of the present invention to enhance the expression of the gene of interest.

As used herein, the term "DC-chol" means a cationic liposome containing cationic cholesterol derivatives. The "DC-chol" molecule includes a tertiary amino group, a medium length spacer arm (two atoms) and a carbamoyl linker bond (Gao et al., Biochem. Biophys. Res, Commun., 179:280-285, 1991).

As used herein, "SF-chol" is defined as a type of cationic liposome.

As used herein, the term "biologically active" used in relation to liposomes denotes the ability to introduce functional DNA and/or proteins into the target cell.

As used herein, the term "biologically active" in reference to a nucleic acid, protein, protein fragment or derivative thereof is defined as an ability of the nucleic acid or amino acid sequence to mimic a known biological function elicited by the wild type form of the nucleic acid or protein.

As used herein, the term "maintenance", when used in the context of liposome delivery, denotes the ability of the introduced DNA to remain present in the cell. When used in other contexts, it means the ability of targeted DNA to remain present in the targeted cell or tissue so as to impart a therapeutic effect.

Bioadhesive Material

The therapeutic somatic cell may be fully or partially surrounded by bio-adhesive material. The bioadhesive material may affect the release profile of the therapeutic substance, and therefore the amount of the admixed bioadhesive material should not hinder or adversely alter the desired release profile of the therapeutic substance.

In addition to having adhesive properties, suitable bioadhesive materials should be bio-compatible, that is non-toxic, non-inflammatory, substantially non-immunogenic and hemo-compatible in the amounts employed.

Bio-adhesive materials can either have non-specific or specific binding properties. Bio-adhesive materials with non-specific binding properties will adhere generally to the cells and the components of the extracellular matrix that form the tissue at the treatment site, through, for example, charge interactions. Examples of bio-adhesive material with non-specific binding properties include, but are not limited to, CARBOPOL® (BF Goodrich Performance Materials, Cleveland, Ohio) polymers, homopolymers and copolymers. The CARBOPOL® polymers include high molecular weight, crosslinked, acrylic acid-based polymers. CARBOPOL® homopolymers include polymers of acrylic acid crosslinked with allyl sucrose or allylpentaerythritol. CARBOPOL® copolymers include polymers of acrylic acid, modified by long chain (C10-C30) alkyl acrylates, and crosslinked with allylpentaerythritol. Other examples include, Carbopol-poloxamer gels, hydroxypropylmethylcellulose, sodium carboxymethyl cellulose, Guar gum, polyvinyl pyrrolidone, chitosan, polyacrylic acid, hydroxypropyl cellulose, polycarbophil, sodium starch glycolate, alginate, and their mixtures and/or copolymers, as well as mixtures, copolymers or graft constructs with polyethylene glycol.

Bio-adhesive materials with specific binding properties adhere to tissue through specific intermolecular interactions with molecules exposed on the surface of the cells and matrix of the tissue at the treatment site. Examples of bio-adhesive materials with specific binding properties include, but are not limited to, lectins, ligands and antibodies to receptor proteins such as cell adhesion molecules and integrins, and albumin.

The particular bio-adhesive material will depend on the intended use and placement of the somatic cells, and in particular, the characteristics of the treatment site to which the cells need to adhere. For example, in cartilaginous or bony areas, buffy coat may be effectively used as an adhesive material, which may preferentially bind to such a solid or semi-solid surface. It is also contemplated that if the target tissue area has a positive charge, then a negatively charged polymeric molecule may be used to aid in the adhesiveness of the therapeutic somatic cells to the target tissue, and vice versa.

If a more specific and directed attachment of the somatic cells to a particular treatment site is desired, a bio-adhesive material with specific binding properties can be chosen for use in the carrier composition. For instance, a bio-adhesive material that binds to molecules exposed only on tissues in specific regions of the body can be used, thus directing the somatic cells to bind to those tissues. Alternatively, if the treatment site is a region of tissue that is diseased or injured, the somatic cells can be targeted to the treatment site by using a bio-adhesive material that binds to molecules that are exposed on that region of tissue due to the disease or injury.

Many components on cell surfaces are glycosylated and have exposed sugar moieties. Lectins are proteins or glycoprotein conjugates that bind to sugar moieties, and therefore, lectins will bind to glycosylated cell surface. If the target treatment site is the heavily glycosylated cells, lectins can be used as a bio-adhesive material that will adhere to the tissue. Lectins are also advantageous because they are generally non-immunogenic. Examples of lectins include, but are not limited to, *Lycopersicon eculantum* agglutinin, wheat germ agglutinin, *Urtica dioica* agglutinin, peanut agglutinin, tomato lectin, and *Ulex europaeus* isoagglutinin.

Receptor proteins known as adhesion molecules are also exposed on the surface of cells. Adhesion molecules mediate cell-cell binding by specifically recognizing and binding to molecules on the surface of other cells. Thus, ligands or antibodies that bind to adhesion molecules exposed on the surface of cells at a particular treatment site can be used as a specific bio-adhesive material to a treatment site.

In one embodiment, a bio-adhesive mixture may be made of those having non-specific binding properties and those bio-adhesive material having specific binding properties. Such a mixture may improve adhesion of therapeutic somatic cell-bioadhesive mixture to a particular treatment site by using, for example, both non-specific charge interactions and specific intermolecular interactions between the bio-adhesive materials and the tissue at the treatment site.

In accordance with an embodiment of the present invention, the above-described bioadhesive-somatic cell mixture may be delivered to a desired treatment site, which is typically an internal body tissue including, but not limited to, a joint space. The bioadhesive-somatic cell may be delivered using any apparatus or technique, such as by injection, so long as the contents are effectively delivered to or near the target tissue.

In another aspect, the invention is directed to using a composition comprised of fibrinogen and thrombin, preferably from a human blood serum. The composition may act like a liquid-type glue when fibrinogen and thrombin solutions are mixed. Further, if the fibrinogen and thrombin are isolated from human serum, the composition should be non-toxic. Such a composition may be commercially available through for example Greenplast™ (Greencross, Korea). Without being limited to any specific process. Without being bound by any particular process of preparing the composition, an example may be as follows:

1. Mix fibrinogen powder (126-256 mg) with aprotinin solution (1.1 ml) using a sterile syringe.
2. Mix thrombin powder (5-11 mg) with NaCl solution (2.5 ml) using a sterile syringe.
3. After dissolving fibrinogen and thrombin in each solution, two solutions are mixed with about 1:1 ratio to form the composition.

Up to at least about a 1:100 dilution of the composition was mixed with cells for injection or loading to effect cartilage regeneration, and resulted in adhesiveness.

Buffy Coat

Buffy coat may be mixed with therapeutic somatic cells before administering the mixture to a site in the body that would benefit from the expression of the therapeutic gene product made from the therapeutic somatic cells. Buffy coat possesses the physical property of being adhering to solid substrates, such as bone and cartilage, as well as semi-solid substrates such as muscle and other tissue, and thus may be used to provide a type of temporary "glue" to hold the therapeutic somatic cell in place at the site of administration so that localized delivery of the therapeutic gene product is achieved.

In a particular embodiment of the invention, buffy coat may be mixed with connective tissue cells that are then injected into the joint space so that a therapeutic gene, such as a cytokine is expressed resulting in a prolonged and effective delivery of the gene product to regenerate cartilage or bone. Such a method is effective for treating osteoarthritis.

Buffy coat is the middle layer in the centrifuge tube when a sample of blood is centrifuged. Top layer is plasma, and the bottom layer contains erythrocytes. However, buffy coat contains leukocytes and platelets. There are various methods of purifying the contents of the buffy coat layer. According to the present invention, this layer may be extracted from a blood sample and mixed with cells that are used in somatic cell therapy protocols. Without being bound by any theory or mechanism of action, it is believed that the inclusion of purified buffy coat with the cells that are administered to a mammalian host results in greater efficiency of expression of the genes at the site of administration because buffy coat assists in binding, fixing or detaining the cells to physiological structure within the mammalian host such as a bone or cartilage so that these cells are expressed.

There are no limits as to how much of the purified buffy coat may be added to the cells before administration of the composition to a mammalian host, so long as the amount is effective to substantially increase the effectiveness of the therapy. In one embodiment, as the cells are related to cartilage generation, the amount of buffy coat added to the cells is effective to generate cartilage. Thus, the ratio of amount of buffy coat to cells may be in the range of about 1-5 to 1 by volume percent of the injectable composition. Typically, the range may include about 1-3 to 1. In particular, the range may be about 1 to 1 in terms of the volume of buffy coat and cells injected.

Without being limited in any way to the preparation method for buffy coat, one way that buffy coat may be made is by centrifuging the anti-coagulated blood in a narrow test tube, then carefully removing as much as possible of the plasma without disturbing the buffy coat. Buffered 2% Glutaraldehyde is then very gently layered on top and the tube left to stand in the fridge for about a couple of hours. This gives a buffy coat which is embedded in solid plasma and can be removed from the tube with the help of a thin wooden stick or similar object. The resultant disk can then be trimmed and the pieces processed to resin for use with normal tissue. Then, the slender tube is cut with a razor blade above and below the buffy coat (on a piece of Parafilm), making a short log with open ends. Then, with a paper clip or applicator stick (depending on the diameter of the tube) the packed buffy coat is pushed out. 1% molten agar is sometimes used to keep it together. The pellet is then processed. The components of a buffy coat are not well characterized, but the buffy coat of the present invention encompasses the middle layer of a centrifuged blood sample.

Gene Therapy

The bioadhesive material of the invention may be mixed with any cell that may be administered to a mammalian host for somatic cell gene therapy. In particular, the buffy coat may be used with connective tissue cells, and in particular cartilage generating cells, such as fibroblasts and chondrocytes. The bioadhesive material of the invention may be mixed with a further mixture of cells that have been transfected or transduced with a gene encoding a cytokine and cells that have not been so engineered.

In the context that the buffy coat is used with cytokine producing cells in treating a cartilaginous defect, the combination is more adhesive to the defect than with cells alone. Thus, the buffy coat method provides greater independence between the location of administration of the cell-buffy coat combination and the location of the defect.

The cell-buffy coat combination also provides a higher success rate for the generation of cartilage in animal tests. Moreover, the average quality of newly generated cartilage is substantially better than from injecting cells alone. In other words, the percentage of normal-like cartilage generated was greater when the cell-buffy coat combination composition was used. Thus, the amount of fibrous cartilage observed was lower for the cell-buffy coat composition than using cells alone.

The present invention discloses ex vivo and in vivo techniques for delivery of a DNA sequence of interest to the connective tissue cells of the mammalian host. The ex vivo technique involves culture of target connective tissue cells, in vitro transfection of the DNA sequence, DNA vector or other delivery vehicle of interest into the connective tissue cells, followed by transplantation of the modified connective tissue cells to the target joint of the mammalian host, so as to effect in vivo expression of the gene product of interest.

It is to be understood that while it is possible that substances such as a scaffolding or a framework as well as various extraneous tissues may be implanted together in the gene therapy protocol of the present invention, it is also possible that such scaffolding or tissue not be included in the injection system of the invention. In a preferred embodiment, in a cell-mediated gene therapy or somatic cell therapy, the invention is directed to a simple method of injecting a population of transfected or transduced connective tissue cells to the joint space so that the exogenous TGF superfamily protein is expressed in the joint space.

One ex vivo method of treating a connective tissue disorder disclosed throughout this specification comprises initially generating a recombinant viral or plasmid vector which contains a DNA sequence encoding a protein or biologically active fragment thereof. This recombinant vector is then used to infect or transfect a population of in vitro cultured connective tissue cells, resulting in a population of connective cells containing the vector. These connective tissue cells together with buffy coat are then transplanted to a target joint space of a mammalian host either as a mixture of transfected and untransfected cells or separately into the joint space so as to cause a mixture of cell types inside the joint, thus effecting subsequent expression of the protein or protein fragment within the joint space. Expression of this DNA sequence of interest is useful in substantially reducing at least one deleterious joint pathology associated with a connective tissue disorder.

It will be understood by the artisan of ordinary skill that the source of cells for treating a human patient may be the patient's own connective tissue cells, such as autologous fibroblast or chondrocyte cells, but that allogeneic cells as well as xenogeneic cells may also be used without regard to the histocompatibility of the cells.

More specifically, this method includes employing as the gene a gene capable of encoding a member of the transforming growth factor β superfamily, or a biologically active derivative or fragment thereof and a selectable marker, or a biologically active derivative or fragment thereof.

A further embodiment of the present invention includes employing as the gene a gene capable of encoding at least one member of the transforming growth factor β superfamily or a biologically active derivative or fragment thereof, and employing as the DNA plasmid vector any DNA plasmid vector known to one of ordinary skill in the art capable of stable maintenance within the targeted cell or tissue upon delivery, regardless of the method of delivery utilized.

Another embodiment of this invention provides a method for introducing at least one gene encoding a product into at least one cell of a connective tissue for use in treating the mammalian host. This method includes employing non-viral means for introducing the gene coding for the product into the connective tissue cell. More specifically, this method includes a liposome encapsulation, calcium phosphate coprecipitation, electroporation, or DEAE-dextran mediation, and includes employing as the gene a gene capable of encoding a member of transforming growth factor superfamily or biologically active derivative or fragment thereof, and a selectable marker, or biologically active derivative or fragment thereof.

Another embodiment of this invention provides an additional method for introducing at least one gene encoding a product into at least one cell of a connective tissue for use in treating the mammalian host. This additional method includes employing the biologic means of utilizing a virus to deliver the DNA vector molecule to the target cell or tissue. Preferably, the virus is a pseudo-virus, the genome having been altered such that the pseudovirus is capable only of delivery and stable maintenance within the target cell, but not retaining an ability to replicate within the target cell or tissue. The altered viral genome is further manipulated by recombinant DNA techniques such that the viral genome acts as a DNA vector molecule which contains the heterologous gene of interest to be expressed within the target cell or tissue.

A preferred embodiment of the invention is a method of delivering TGF-β or BMP to a target joint space by delivering the TGF-β or BMP gene to the connective tissue of a mammalian host through use of a retroviral vector with the ex vivo technique disclosed within this specification. In other words, a DNA sequence of interest encoding a functional TGF-β or BMP protein or protein fragment is subcloned into a retroviral vector of choice. The recombinant viral vector is then grown to adequate titer and used to infect in vitro cultured connective tissue cells, and the transduced connective tissue cells, preferably autografted cells, are mixed with buffy coat and are transplanted into the joint of interest with optionally an untransfected sample of connective tissue cell such as chondrocytes preferably by intra-articular injection.

In a preferred embodiment, fibroblasts are cultured in vitro for subsequent utilization as a delivery system for gene therapy. It will be apparent that Applicants are not limited to the use of the specific connective tissue disclosed. It would be possible to utilize other tissue sources for in vitro culture techniques. The method of using the gene of this invention may be employed both prophylactically and in the therapeutic treatment of arthritis. It will also be apparent that Applicants are not limited to prophylactic or therapeutic applications in treating only the knee joint. It would be possible to utilize the present invention either prophylactically or therapeutically to treat arthritis in any susceptible joint.

In another embodiment of this invention, a compound for parenteral administration to a patient in a therapeutically effective amount is provided that contains a gene encoding a TGF-β superfamily protein and a suitable pharmaceutical carrier.

Another embodiment of this invention provides for a compound for parenteral administration to a patient in a prophylactically effective amount that includes a gene encoding a TGF-β superfamily protein and a suitable pharmaceutical carrier.

In a further embodiment of this invention the cells are stored before administration to the joint space. The transfected or transduced cells alone may be stored, or optionally the untransfected helper cells alone may be stored, or the mixture may be stored, but not necessarily simultaneously. In addition, the duration of storage need not be for the same time period. Thus, the individually stored cells may be optionally mixed prior to injection. Alternatively, the cells may be stored and injected separately to form a mixture of cells within the joint space. It will be appreciated by those skilled in the art that these cells may be stored frozen in about 10 percent DMSO in liquid nitrogen. In another embodiment, the buffy coat may be included in the storage composition.

Another embodiment of this invention includes a method of introducing at least one gene encoding a product into at least one cell of a connective tissue of a mammalian host for use in treating the mammalian host as hereinbefore described including effecting in vivo the infection of the cell by introducing the viral vector containing the gene coding for the product directly into the mammalian host. Preferably, this method includes effecting the direct introduction into the mammalian host by intra-articular injection. This method includes employing the method to substantially prevent the development of arthritis in a mammalian host having a high susceptibility of developing arthritis. This method also includes employing the method on an arthritic mammalian host for therapeutic use. Further, this method also includes employing the method to repair and regenerate the connective tissue as hereinbefore defined.

It will be appreciated by those skilled in the art, that the viral vectors employing a liposome are not limited by cell division as is required for the retroviruses to effect infection and integration of connective tissue cells. This method employing non-viral means as hereinbefore described includes employing as the gene a gene capable of encoding a member belonging to the TGF-β superfamily and optionally, a selectable marker gene, such as an antibiotic resistance gene. And it is also understood that using a selectable marker gene is not a requirement to practicing the claimed invention.

Another embodiment of the present invention is delivery of a DNA sequence encoding a member of the TGF-β superfamily to the connective tissue of a mammalian host by any of the methods disclosed within this specification so as to effect in vivo expression of collagen to regenerate connective tissue, such as cartilage.

Connective tissues are difficult organs to target therapeutically. Intravenous and oral routes of drug delivery that are known in the art provide poor access to these connective tissues and have the disadvantage of exposing the mammalian host body systemically to the therapeutic agent. More specifically, known intra-articular injection of proteins to joints provides direct access to a joint. However, most of the injected drugs in the form of encapsulated proteins have a short intra-articular half-life. The present invention solves these problems by introducing into the connective tissue of a mammalian host genes coding for proteins that may be used to treat the mammalian host. More specifically, this invention provides a method for introducing into the connective tissue of a mammalian host genes coding for proteins with anti-arthritic properties.

In the Examples provided herein, various cytokine producing cells such as fibroblasts and chondrocytes as well as mixtures of various cell types stimulated collagen synthesis in the joint. Compositions that included buffy coat also showed stimulation of collagen synthesis. In the Examples, the joint was generally injected with about $10^6$ cells/ml concentration. The specimens were harvested from 2 weeks to 12 weeks after injection. The cells move freely within the joint, and move to the area with specific affinity for these cells. The synovium, meniscus and cartilage defect areas may be possible sites for cellular adhesion. At two to twelve weeks after injection, the regenerated tissues were observed in both the partially and completely damaged cartilage defect areas. This specific affinity for the damaged area is another advantage of using mixed cells for clinical application. If degenerative arthritis can be cured with just injection of cells into the joint without including various physical apparatuses such as scaffolding or any other three-dimensional structure, the patients can be treated conveniently without major surgery.

Whatever the mechanism of action is, and without being bound to any particular theory regarding the mechanism of action, the finding of hyaline cartilage synthesis by using the cytokine producing cells, mixed cell compositions and buffy coat containing compositions of the invention indicate that a long duration of high TGF-β or BMP concentration can stimulate hyaline cartilage regeneration. The properties of newly formed tissue were determined by histological methods. Through H & E staining, Mason's trichrome staining and Safranin-O, it was indicated that the newly formed tissue was identical to the surrounding hyaline cartilage.

The following examples are offered by way of illustration of the present invention, and not by way of limitation.

EXAMPLES

Example I

Materials and Methods

Plasmid Construction

To generate the metallothionein expression construct (pM), the metallothionein I promoter (−660/+63) was generated by polymerase chain amplification using genomic DNA using Xba I and Bam HI restriction sites built into the oligonucleotides used for amplification. The amplified fragment was subcloned into Xba I-Bam HI sites of pBluescript (Stratagene, La Jolla, Calif.). The plasmid pmT β1 was generated by subcloning a 1.2-kb Bgl II fragment containing the TGF-β1 coding sequence and a growth hormone poly A site at the 3' end into the Bam HI-Sal I sites of pM. The plasmid pMT-BMP2 was generated by subcloning a 1.2-kb Sal I-Not I fragment containing the BMP2 coding sequence into the Sal I-Not I sites of pMTMLV. pMTMLV vector was derived from the retroviral vector MFG by deleting entire gag and env sequences as well as some of ψ packaging sequence.

Cell Culture and Transfections—The TGF-β1 cDNA was transfected into fibroblasts (NIH 3T3-TGF-β1), human foreskin fibroblasts (human foreskin-TGF-β1), and chondrocytes (hChon-TGF-β1). They were cultured in Dulbecco's Modified Eagle's Medium (GIBCO-BRL, Rockville, Md.) with 10% concentration of fetal bovine serum. The TGF-β1 cDNA sequence was added into the pmTβ1 vector with a metallothionein gene promoter. A neomycin resistance gene sequence was also inserted into the vector.

The calcium phosphate method to insert this vector into the cells was used. To select the cells with the transfected gene sequence, neomycin (300 mg/ml) was added into the medium. Then, the surviving colonies were selected and the expression of TGF-β1 mRNA was confirmed by Northern analysis and TGF-β1 ELISA assay (R & D Systems). The cells with TGF-β1 expression were stored in liquid nitrogen and cultured just before the injection.

Northern Blot analysis—Total RNA was isolated from cells with guanidium isothiocyanate/phenol/chloroform. 10 mg of RNA was electrophoresed on a 1.0% agarose gel containing 0.66M formaldehyde, transferred to a DURALON-UV membrane, and cross linked with a UV STRATALINKER (STRATAGENE). Blots were prehybridized and hybridized in a solution of 1% bovine serum albumin, 7% (w/v) SDS, 0.5 M sodium phosphate, and 1 mM EDTA at 65° C. Hybridized blots were washed in 0.1% SDS, 1×SSC for 20 minute periods at 50° C. before film exposure. RNA blots were hybridized with 32P-labelled cDNA probes for human TGF-β1. A probe for β-actin was used to control for sample loading.

Injection of cells into rabbit—New Zealand white rabbits weighing 2.0-2.5 kg were selected as the animal model. After anesthetization with ketamine and roumpun, each rabbit was draped in a sterile manner. The knee joint was exposed, and partial and complete cartilage defects were made with a knife. The partial defects were made on the hyaline cartilage layer with caution not to expose the subchondral bone. The complete defects were made to expose the subchondral bone after removing all of the hyaline cartilage. After closing the surgical wound, the cells with $10^6$ cells/ml concentration were injected intraarticularly, and zinc sulfate was added to the drinking water when TGF-β1 bearing cells were assayed.

Histological examination—After investigating the knee joints, the specimens were fixed in formalin and decalcified with nitric acid. They were embedded in a paraffin block and cut into 0.8 mm thickness slices. Hematoxilin-eosine, Safranin-O and Mason's multichrome staining were utilized to observe the regenerated tissue microscopically.

Buffy Coat Preparation—After centrifuging the anti-coagulated blood, the plasma is carefully removed as much as possible. The buffy coat layer is then removed without disturbing the bottom layer into a clean tube and washed in 1×PBS three to four times.

Example II

Experimental Methods and Results

Stable cell line—Transfection was carried out by using the calcium phosphate coprecipitation method (FIGS. 1A-1C). About 80% of the surviving colonies expressed the transgene mRNA. These selected TGF-β1-producing cells were incubated in a zinc sulfate solution. When the cells were cultured in 100 mM zinc sulfate solution, they produced mRNA. The TGF-β secretion rate was about 32 ng/$10^6$ cells/24 hr.

To test and confirm the production of biologically active BMP2 proteins by NIH3T3 fibroblast cells infected with retroviral vectors containing BMP2 cDNAs, alkaline phosphatase (ALP) activity assays were carried out with control NIH3T3-metallothionein (FIG. 1B) and NIH3T3-BMP2 cells (FIG. 1C). Blue color in FIG. 1C shows expression of BMP2 protein.

$1.5 \times 10^6$ NIH3T3 cells were grown overnight in a 6 well tissue culture plate. $0.5 \times 10^5$ indicating cells (MC3T3E1) were placed in tissue culture inserts and grown overnight. Culture medium was aspirated from the culture insert and the culture insert transferred into a 6 well plate and incubated for 48-72 hours. Culture medium was aspirated from the culture inserts. 5 ml of 1× phosphate buffered saline (PBS) was added to wash the cells. 4 ml of 3.7% formaldehyde/1×PBS solution was added to each insert, and the cells were fixed for 20 min at 4° C. Cells were washed twice with 1×PBS. 3 ml of ALP staining solution was added to each culture insert, and the culture insert was incubated for about 20 min to 1 hr at room temperature in the dark for blue color development. ALP staining solution is 0.1 mg/ml naphthol AS-MX phosphate (Sigma N5000), 0.5% N-dimethylformamide (Sigma D8654), 2 mM $MgCl_2$, 0.3 mg/ml Fast Blue BB salt (Sigma F3378) in 0.1 M Tris-HCl, pH 8.5.

Figure 2:
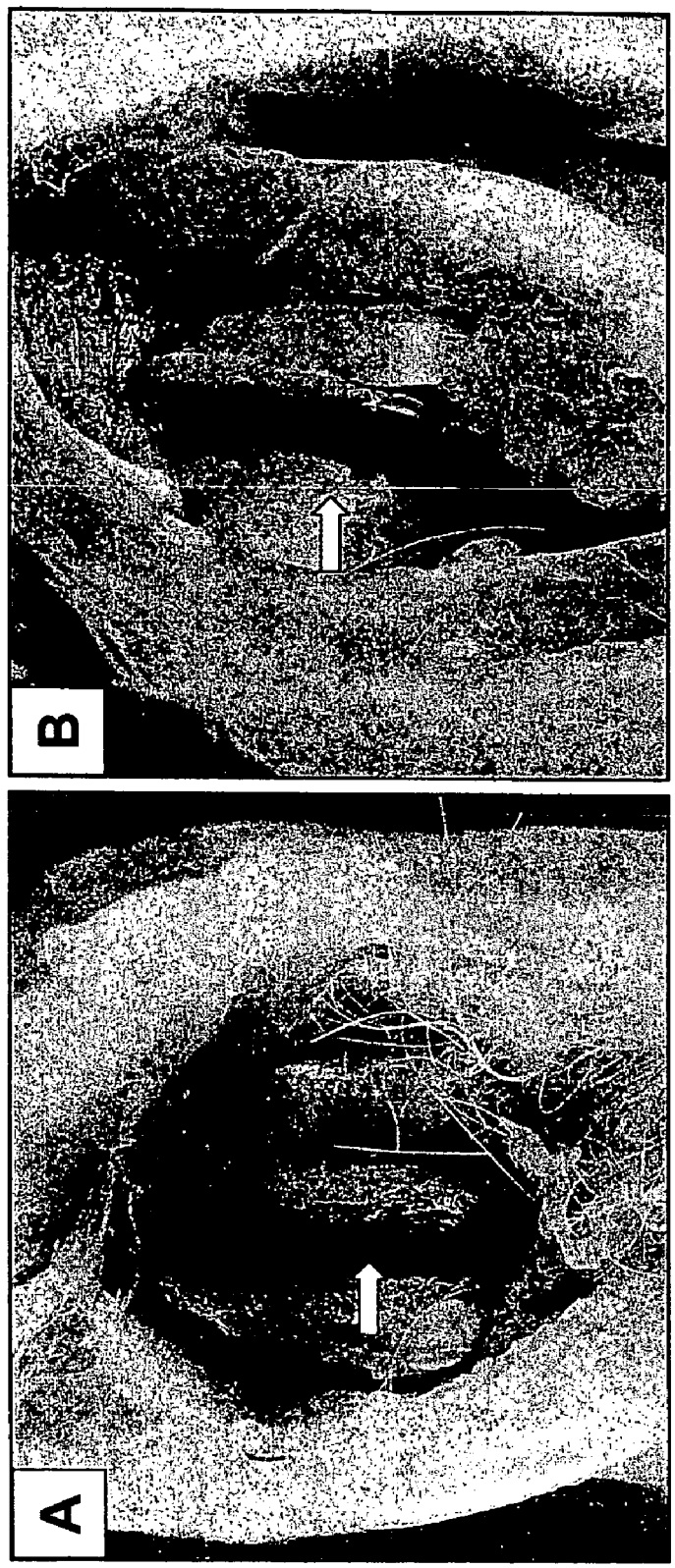
FIGS. 2A-2B show gross findings of regenerated cartilage.
Figure 3:
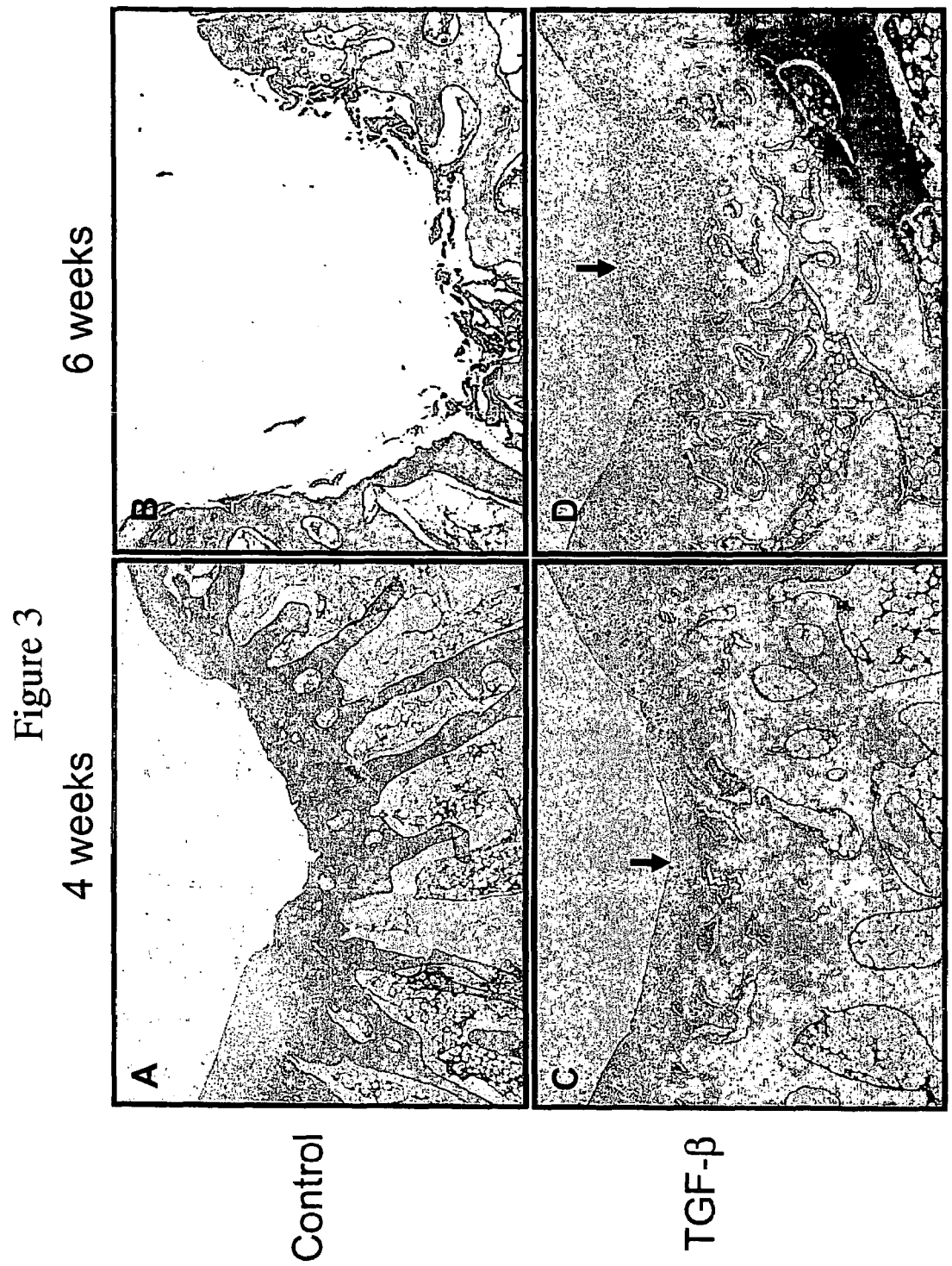
FIGS. 3A-3D show microscopic findings of regenerated cartilage (×200).
Figure 4:
FIGS. 4A-4B show immunohistochemical analysis for TGF-β1 expression in rabbit joint ×200. Brown immunoperoxidase reaction product indicates high levels of recombinant TGF-β1 expression in the NIH 3T3-TGF-β1 cells (FIG. 4B).

Regeneration of Rabbit Articular Cartilage Defect—After making partial and complete cartilage defects, 0.3 ml of $10^6$ cells/ml of the NIH 3T3-TGF-β1 cells were injected into knee joints. The joint was examined 2 to 6 weeks after injection. In partially damaged cartilage, newly formed hyaline cartilage was found; two weeks after injection, hyaline cartilage appeared and six weeks after injection, the cartilage defects were covered by hyaline cartilage (FIG. 2). The thickness of the regenerated cartilage became thicker as time passed (FIG. 3). The injected cells secreted TGF-β1, that could be observed by immunohistochemical staining with TGF-β1 antibody (FIG. 3). The contralateral side injected with normal fibroblasts without TGF-β1 transfection was not covered by hyaline cartilage. In the partially damaged area, the regenerated hyaline cartilage was colored red in Safranin-O staining (FIG. 4). The depth of newly formed cartilage was almost the same as that of the defect. This finding suggests that the injected cells activate the surrounding normal cartilage cells through a paracrine mode of action.

Figure 5:
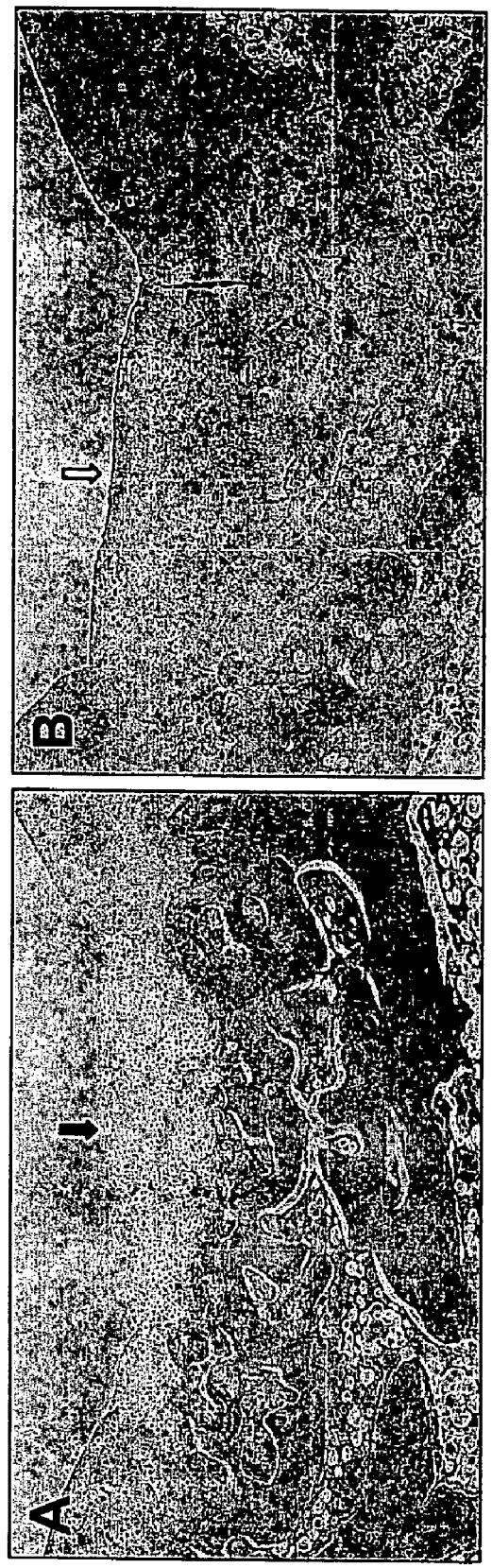
FIGS. 5A-5B show microscopic findings (×200) of regenerated tissues with H&E staining (A) and Safranin-O staining (B).

When NIH3T3-TGF-β1 cells alone were used, the regenerated tissues in completely damaged cartilage were not hyaline cartilage but fibrous collagen. Their color in Safranin-O staining was white instead of the red color obtained with hyaline cartilage (FIG. 5). The cartilage was covered by fibrous tissue, which means that these cells were activated only by the autocrine mode. The surrounding osteocytes, which can be stimulated by TGF-β1, appeared to have been blocked from being stimulated by TGF-β1 by the presence of a thick calcified bone matrix. The injected cells may have been unable to stimulate the osteocytes because of this barrier.

Example III

Either control NIH3T3 or NIH3T3-TGF-β1 cells (5-7×$10^5$) were irradiated with 6000 rad. and injected into rabbit knee joints. These irradiated cells died completely in 3 weeks in a tissue culture dish. The injection procedure was the same as in the previous protocol with untreated cells. The knee joints were harvested at 3 or 6 weeks post injection. The specimens were fixed in formalin and decalcified with nitric acid. Sections of the specimens were made and embedded with paraffin and then cut into 0.5 mm thickness slices. In FIG. 6, Safranin-O staining (A-D & A'-D') and Hematoxilin-Eosine staining (E-F & E'-F') were done in the sections to observe the regenerated cartilage tissue microscopically. (Original magnification: (A, B, A' & B')×12.5; (C-F & C'-F')×400).

Example IV

Figure 7:
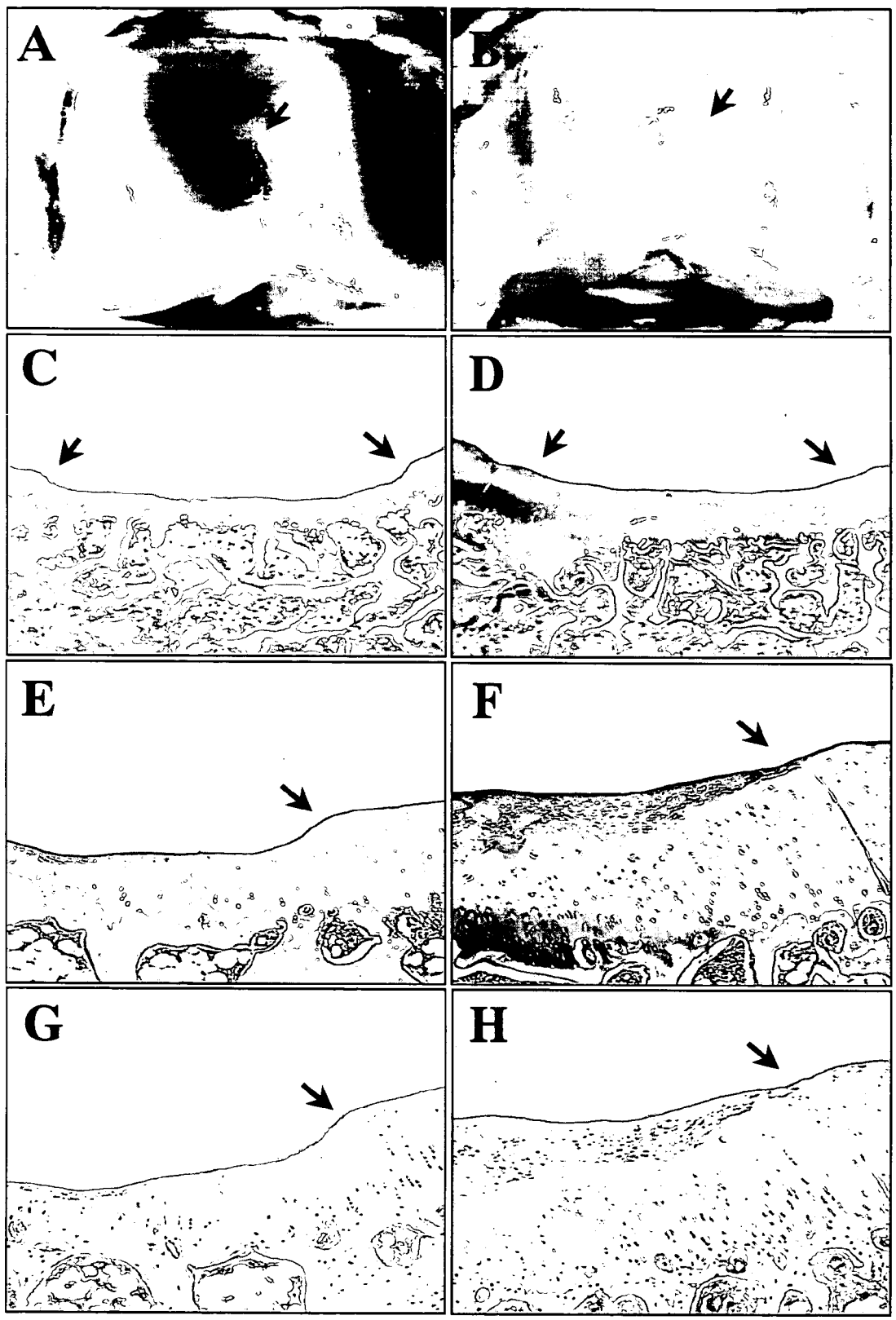
FIGS. 7A-7H show regeneration of cartilage with human foreskin fibroblast cells producing TGF-β1.

Either control human foreskin fibroblast (hFSF) or hFSF-TGF-β1 cells were injected into the rabbit knee joint containing a partial cartilage defect (3 mm×5 mm, 1.5 mm deep) on the femoral condyle. These cells (0.5 ml of 2×106 cells/ml) were injected as in the previous protocol, or 20-25 ml cells of the same concentration were loaded to the top of the defect. In the latter case, the cells were left in the defect for 15-20 min to let them settle down at the bottom of the defect before suturing. In both cases, a similar level of cartilage regeneration was obtained. The specimens were harvested at 6 weeks after injection and observed microscopically. FIGS. 7A & B show pictures of the femoral condyles 6 weeks post injection with either hFSF (A) or hFSF-TGF-β1 cells (B). C. E, & G show Safranin-O staining (C & E) and H&E staining (G) of sections from the femoral condyle injected with control hFSF cells. D, F, & H show Safranin-O staining (D & F) and H&E staining (H) of sections from the femoral condyle injected with hFSF-TGF-β1 cells. (Original magnification: (C & D)×12.5; (E-H)×400).

Example V

Figure 8:
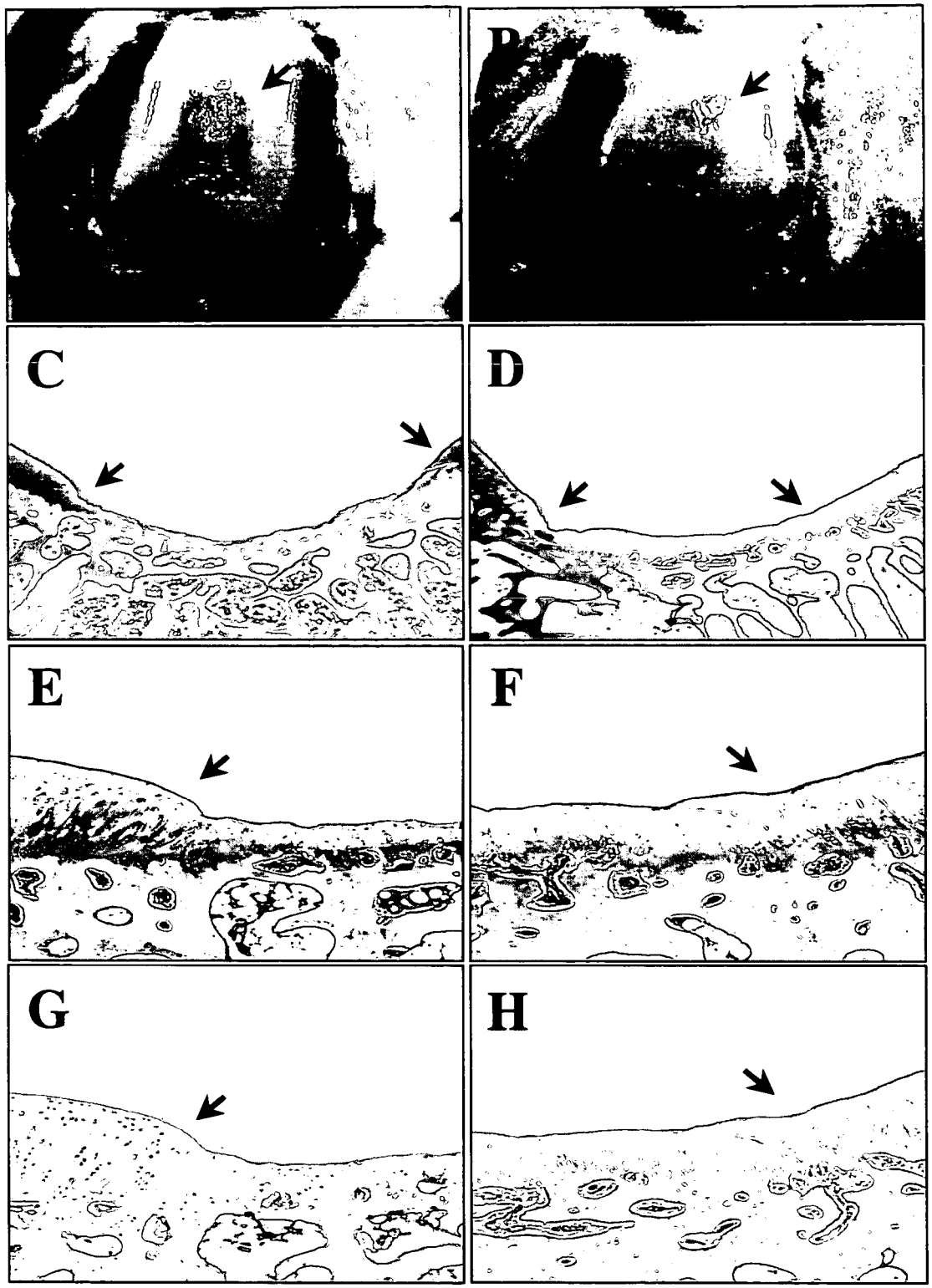
FIGS. 8A-8H show regeneration of cartilage with NIH3T3-TGF-β1 cells in a dog model.

Either control NIH3T3 or NIH3T3-TGF-β1 cells was injected into the dog knee joint containing a partial cartilage defect (6 mm×6 mm, 2 mm deep) on the femoral condyle. These cells (4 ml of 2×106 cells/ml) were injected as in the previous protocol, or 30-35 ml cells of the same concentration were loaded to the top of the defect. In the latter case, the cells were left in the defect for 15-20 min to let them settle down at the bottom of the defect before suturing. In both cases, a similar level of cartilage regeneration was obtained. The specimens were harvested at 6 weeks post injection and observed microscopically. FIGS. 8, A & B show pictures of the femoral condyles 6 weeks post injection with either NIH3T3 cells (A) or NIH3T3-TGF-β1 cells (B). C, E, & G show Safranin-O staining (C & E) and H&E staining (G) of sections from the femoral condyle injected with control NIH3T3 cells. D, F, & H show Safranin-O staining (D & F) and H&E staining (H) of sections from the femoral condyle injected with NIH3T3-TGF-β1 cells. (Original magnification: (C & D)×12.5; (E-H)×400.)

Example VI

Figure 9:
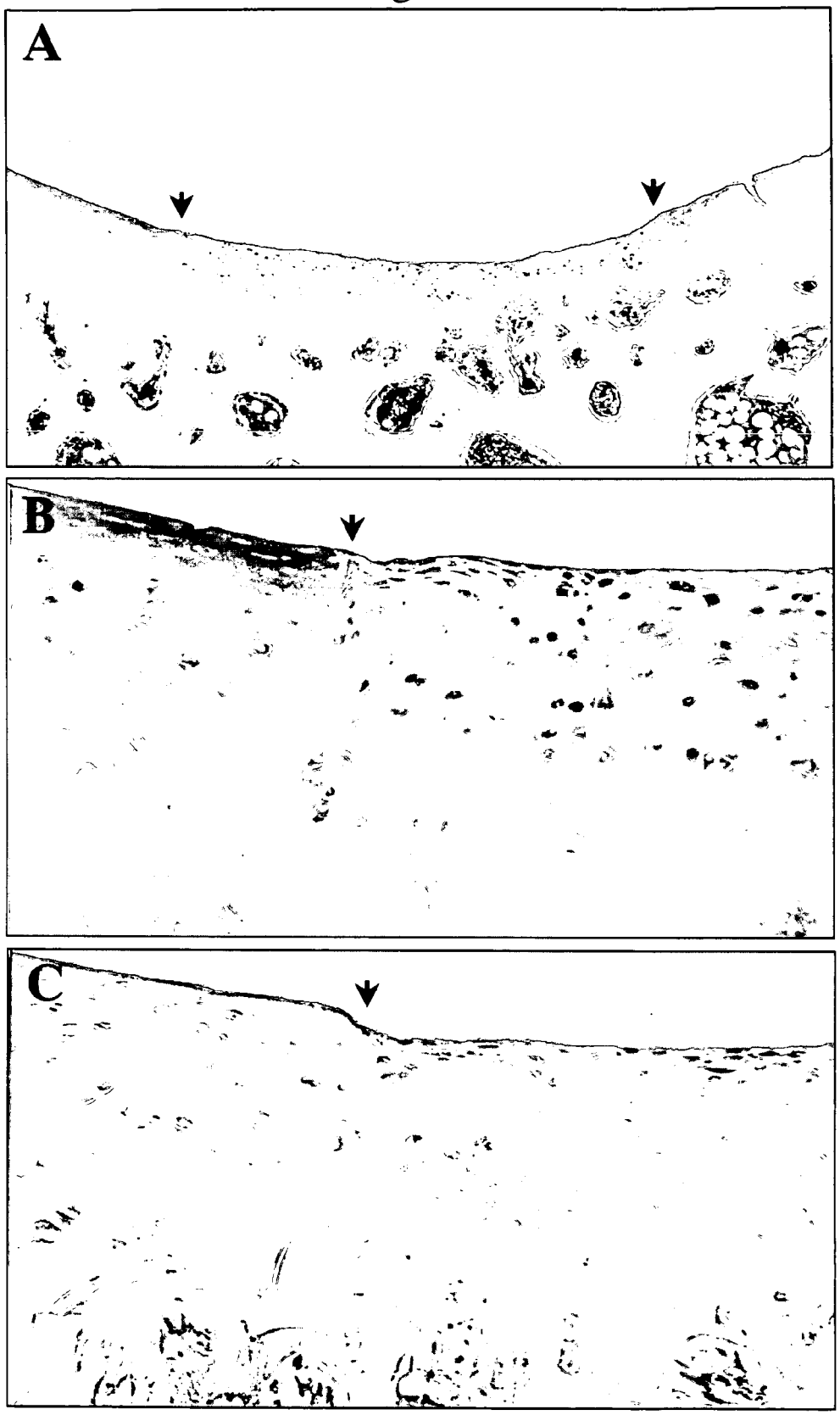
FIGS. 9A-9C show immunohistochemical staining of regenerated cartilage with TGF-β1 antibody at 3 weeks after injection of TGF-β1 producing fibroblast cells.

To investigate the expression of TGF-β1 protein in the regenerated cartilage tissue, immunohistochemical staining of repair tissue after 3 weeks post injection was performed with TGF-β1 antibody. The results showed a high level of TGF-β1 protein expression only in the cells of the regenerated cartilage, many of which appear to be newly made chondrocytes (FIGS. 9, A & B). No staining was seen in the section from the same tissue probed with the secondary antibody alone (FIG. 9, C). (Original magnification: A ×12.5; (B-C)×40).

After harvesting the rabbit knee joint, the specimen was fixed in formalin and decalcified with nitric acid. Sections of the specimen were made and embedded with paraffin and then cut into 0.8 mm thickness slices. The sections were deparaffinized and hydrated by sequential incubations in xylene and ethanol. After washing in 1×PBS for 2 min, the sections were blocked with 3% $H_2O_2$ for 10 min. The primary antibody against TGF-β1 protein was applied to the sections and incubated for 1 hour. The control sections were incubated in 1×PBS without the primary antibody at this step. The sections were washed and blocked with 5% milk in 1×PBS for 20 min before incubating with the HRP-conjugated secondary antibody. Chromogen reaction was done with 0.05% diaminobenzidine (DAB) in 1×PBS for 5 min. The sections were then stained with hematoxylin and mounted.

The immunohistochemical staining data in this study and the data in dog model study suggest a possibility for the molecular mechanism of regeneration of hyaline cartilage with the current cell-therapy method. The fibroblast cells injected into the knee joint may have somehow differentiated to chondrocytes through an unknown pathway, like a "reverse differentiation" type of process. This pathway was probably initiated by TGF-β1 secreted from the injected fibroblasts in vivo, which caused the remaining chondrocytes and the fibroblasts to release various factors to proceed in this pathway as by the paracrine or autocrine mode of TGF-β1 action.

Example VII

Figure 10:
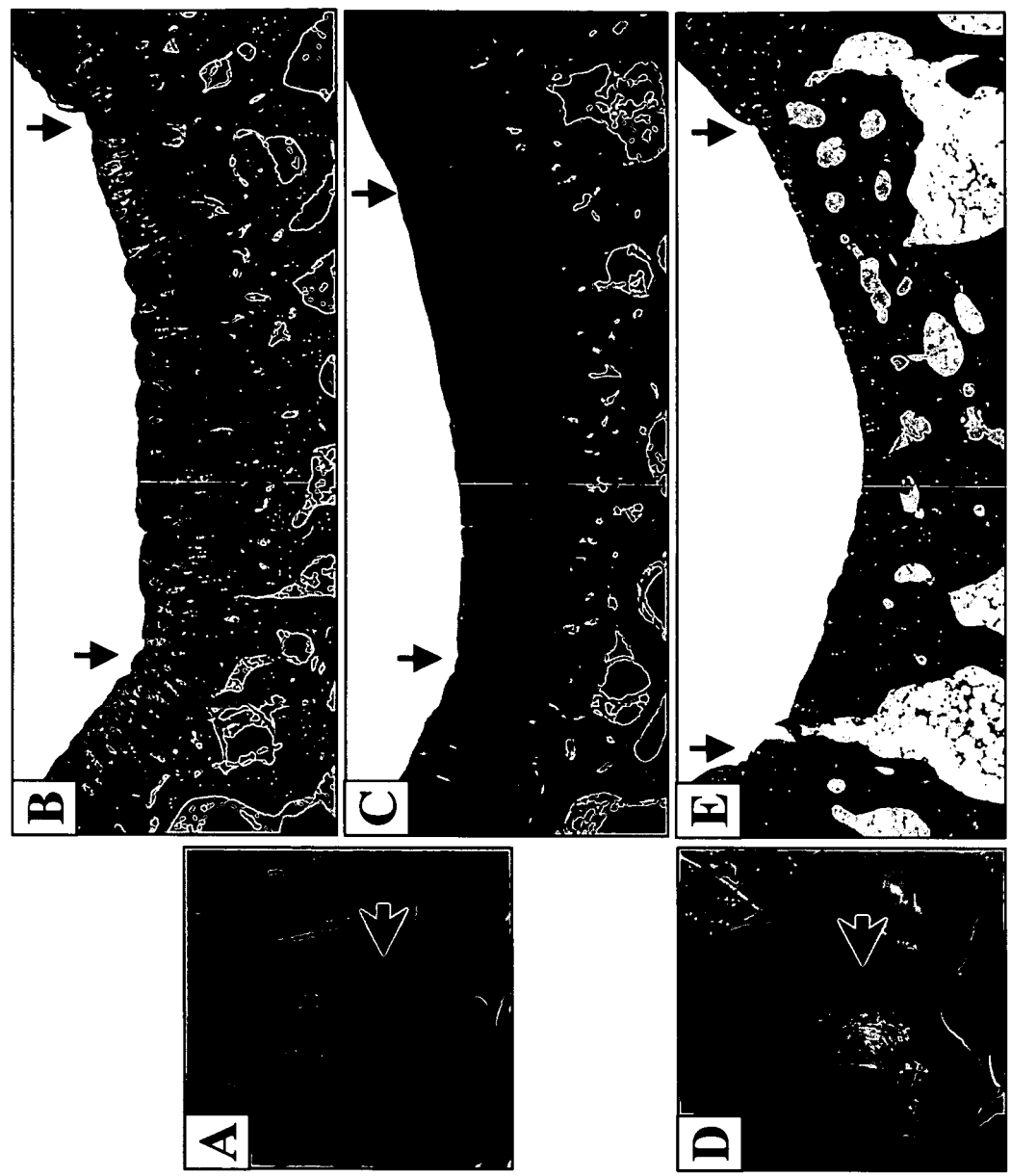
FIGS. 10A-10E show regeneration of cartilage with human chondrocyte cells producing TGF-β1.

Either hChon-TGF-β1 or control hChon cells were injected into the rabbit knee joint containing a partial cartilage defect (3 mm×5 mm, 1.5 mm deep) on the femoral condyle. These cells (15-20 ul of 2×$10^6$ cells/ml) were loaded into the defect. Then the cells were left in the defect for 15-20 min to let them settle down in the defect before suturing. The specimens were harvested at 6 weeks after injection and observed microscopically (FIGS. 10A-E). FIGS. 10A & D show pictures of the femoral condyles 6 weeks after injection with either hChon-TGF-β1 (A) or control hChon (D) cells. FIGS. 10B, C, & E show Mason's Trichrome (B & E) and Safranin-O statining (C) of sections from the femoral condyles injected with either hChon-TGF-β1 (B & C) or control hChon cells (E). [Original magnification: (B, C & E)×12.5].

Example VIII

Regeneration of Rabbit Articular Cartilage Defect—New Zealand white rabbits weighing 2.0-2.5 kg were selected for the animal study. These rabbits were mature and had a tidemark. The knee joint was exposed and a partial cartilage defect (3 mm×6 mm, 1-2 mm deep) or full-thickness defect (3 mm×6 mm, 2-3 mm deep) was made on the hyaline cartilage layer of the femoral condyle with a surgical knife. Either control human chondrocytes (hChon), or mixture of hChon and NIH3T3-TGF-β1 cells, or NIH3T3-BMP-2 cells were injected into the rabbit knee joint with the defect. These cells (15-20 μl of 2×10$^6$ cells/ml) were loaded to the top of the defect and then left in the defect for 15-20 min to allow the cells to permeate the wound before suturing. In the experiment with mixture of hChon and NIH3T3-BMP-2 cells, these cells were injected into the defect 3 weeks after making the defect. The femoral condyles were harvested at 6 or 12 weeks post injection of the cells and examined.

Example IX

Figure 11:
FIGS. 11A-11D show regeneration of cartilage with mixed-cell (human chondrocytes and NIH3T3-TGF-β1 cells) injection in rabbits with a partial defect.

Regeneration Of Cartilage With Mixed-Cell (Human Chondrocytes And NIH3T3-TGF-β1 Cells) Injection In Rabbits With A Partial Defect—Either control hChon or mixture of hChon and NIH3T3-TGF-β1 cells were injected into the rabbit knee joint containing a partial cartilage defect (3 mm×5 mm, 1-2 mm deep) on the femoral condyle. The mixture of cells (15-20 μl of 2×10$^6$ cells/ml, 10:1 ratio of hChon and NIH3T3-TGF-β1) were loaded to the top of the defect and then left in the defect for 15-20 min to allow the cells to permeate the wound before suturing. The specimens were harvested at 6 weeks after injection and observed microscopically. FIGS. 11A & C show pictures of the femoral condyles 6 weeks post injection with either mixture of hChon and NIH3T3-TGF-β1 cells (A) or hChon alone (C). FIGS. 11B & D show Mason's trichrome staining of sections from the femoral condyle injected with either mixture of hChon and NIH3T3-TGF-β1 cells (B) or hChon alone (D). [Original magnification: (B & D)×12.5].

Example X

Figure 12:
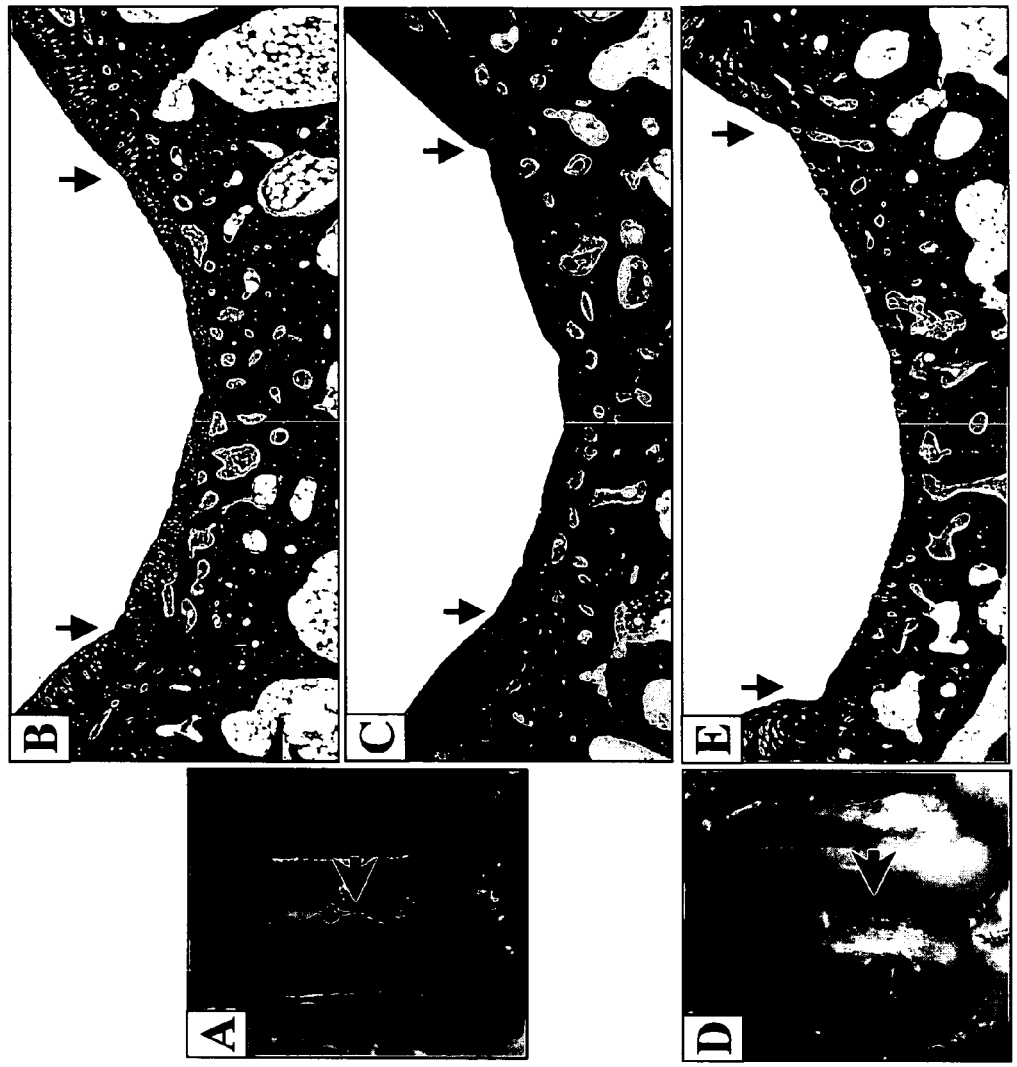
FIGS. 12A-12E show regeneration of cartilage with mixed-cell (human chondrocytes and NIH3T3-TGF-β1 cells) injection in rabbits with a full-thickness defect.

Regeneration Of Cartilage With Mixed-Cell (Human Chondrocytes And NIH3T3-TGF-β1 Cells) Injection In Rabbits With A Full-Thickness Defect—Either control hChon or mixture of hChon and NIH3T3-TGF-β1 cells were injected into the rabbit knee joint containing a full-thickness cartilage defect (3 mm×5 mm, 2-3 mm deep) on the femoral condyle. The mixture of cells (20-25 μl of 2×10$^6$ cells/ml, 10:1 ratio of hChon and NIH3T3-TGF-β1) were loaded to the top of the defect and then left in the defect for 15-20 min to allow the cells to permeate the wound before suturing. The specimens were harvested at 12 weeks after injection and observed microscopically. FIGS. 12A & D show pictures of the femoral condyles 12 weeks post injection with either mixture of hChon and NIH3T3-TGF-β1 cells (A) or hChon alone (D). FIGS. 12B, C & E show Mason's trichrome staining (B & E) and Safranin-O staining (C) of sections from the femoral condyle injected with either mixture of hChon and NIH3T3-TGF-β1 cells (B & C) or hChon alone (E). [Original magnification: (B, C & E)×12.5].

Example XI

Figure 13:
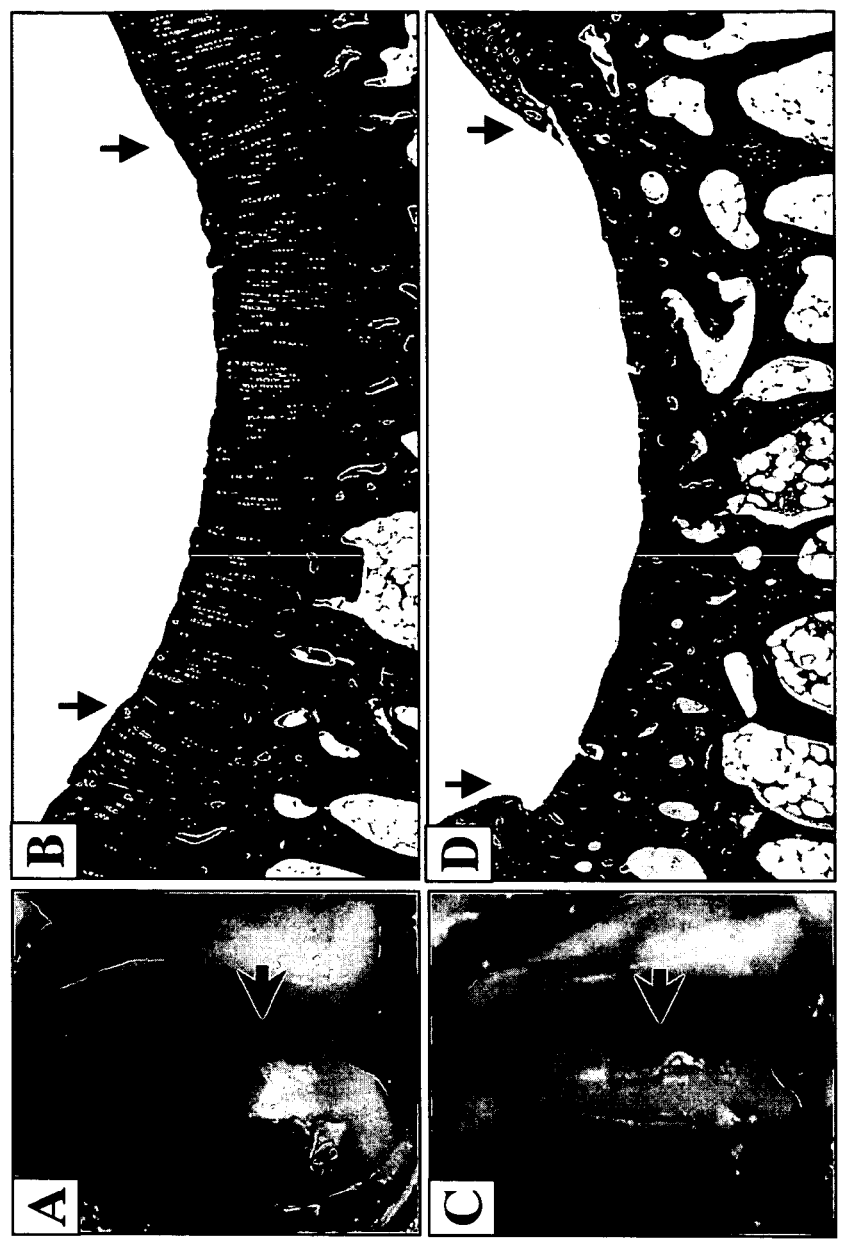
FIGS. 13A-13D show regeneration of cartilage with mixed-cell (human chondrocytes and NIH3T3-BMP-2 cells) injection in rabbits with a partial defect.

Regeneration Of Cartilage With Mixed-Cell (Human Chondrocytes And NIH3T3-BMP-2 Cells) Injection In Rabbits With A Partial Defect—Either control hChon or mixture of hChon and NIH3T3-BMP-2 cells were injected into the rabbit knee joint containing a partial cartilage defect (3 mm×5 mm, 1-2 mm deep) on the femoral condyle. The mixture of cells (15-20 μl of 2×10$^6$ cells/ml, 10:1 ratio of hChon and NIH3T3-BMP-2) were loaded to the top of the defect and then left in the defect for 15-20 min to allow the cells to permeate the wound before suturing. The specimens were harvested at 6 weeks after injection and observed microscopically. FIGS. 13A & C show pictures of the femoral condyles 6 weeks post injection with either mixture of hChon and NIH3T3-BMP-2 cells (A) or hChon alone (C). FIGS. 13B & D show Mason's trichrome staining of sections from the femoral condyle injected with either mixture of hChon and NIH3T3-BMP-2 cells (B) or hChon alone (D). [Original magnification: (B & D)×12.5].

Example XII

Figure 14:
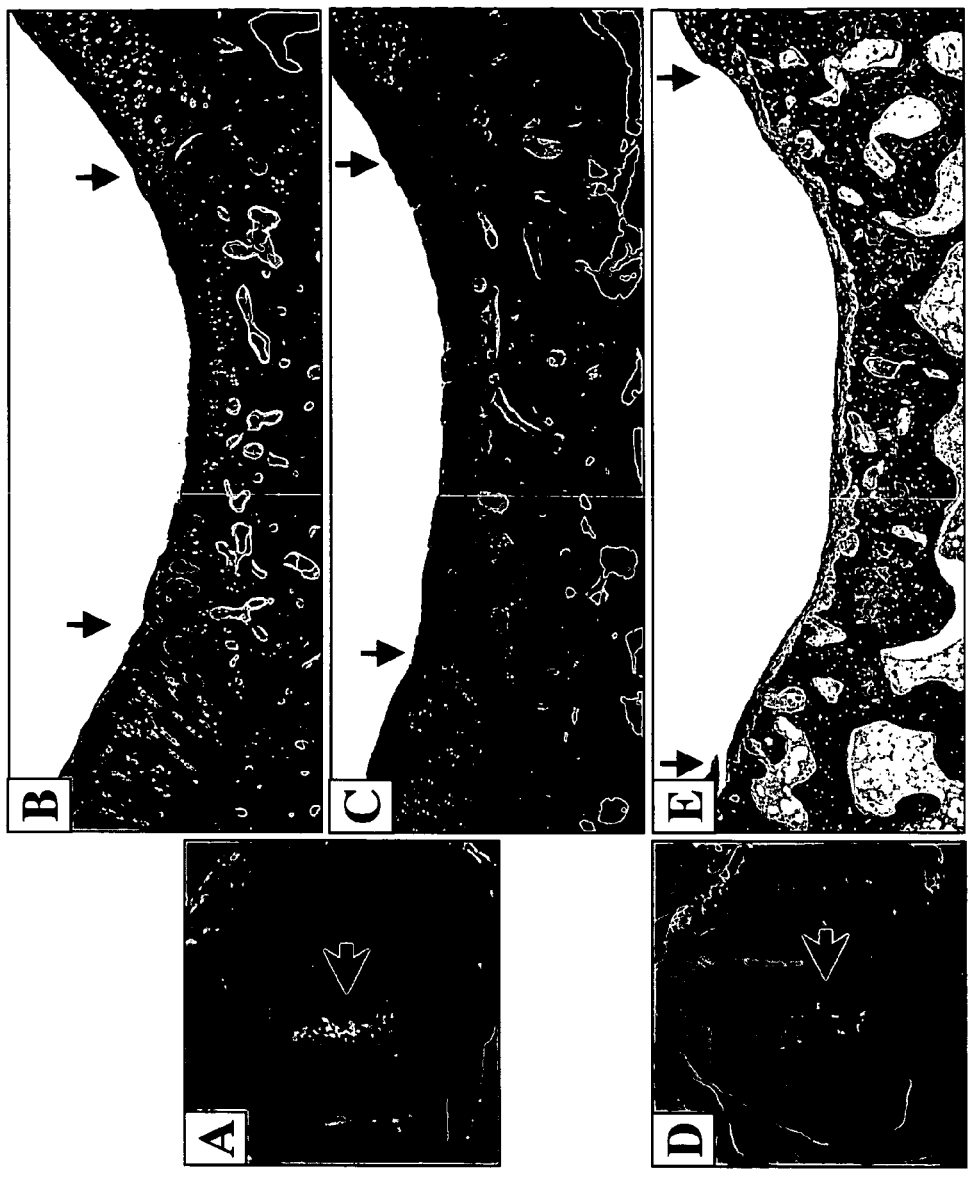
FIGS. 14A-14E show regeneration of cartilage with mixed-cell (human chondrocytes and NIH3T3-BMP-2 cells) injection in rabbits with a full-thickness defect.

Regeneration Of Cartilage With Mixed-Cell (Human Chondrocytes And NIH3T3-BMP-2 Cells) Injection In Rabbits With A Full-Thickness Defect—Either control hChon or mixture of hChon and NIH3T3-BMP-2 cells were injected into the rabbit knee joint containing a full-thickness cartilage defect (3 mm×5 mm, 2-3 mm deep) on the femoral condyle. In this case, the cells were injected 3 weeks after making the defect. The mixture of cells (20-25 μl of 2×10$^6$ cells/ml, 10:1 ratio of hChon and NIH3T3-BMP-2) were loaded to the top of the defect and then left in the defect for 15-20 min to allow the cells to permeate the wound before suturing. The specimens were harvested at 6 weeks after injection and observed microscopically. FIGS. 14A & D show pictures of the femoral condyles 12 weeks post injection with either mixture of hChon and NIH3T3-BMP-2 cells (A) or hChon alone (D). FIGS. 14B, C & E show Mason's trichrome staining (B & E) and Safranin-O staining (C) of sections from the femoral condyle injected with either mixture of hChon and NIH3T3-BMP-2 cells (B & C) or hChon alone (E). [Original magnification: (B, C & E)×12.5].

Example XIII

Figure 15:
FIGS. 15A-15D show regeneration of cartilage with mixed-cell (human chondrocytes and human chondrocyte-TGF-β1 cells) injection in rabbits with a full-thickness defect.

Regeneration Of Cartilage With Mixed-Cell (Human Chondrocytes And Human Chondrocyte-TGF-β1 Cells) Injection In Rabbits With A Full-Thickness Defect—Either control human chondrocytes (hChon) or a mixture of hChon and hChon-TGF-β1 cells was injected into the rabbit knee joint containing a full-thickness cartilage defect (3 mm×5 mm, 2-3 mm deep) on the femoral condyle. The cell mixture (20-25 μl of 2×10$^6$ cells/ml, 1:1 ratio of hChon and hChon-TGF-β1) was loaded to the top of the defect and then left in the defect for 15-20 min to allow the cells to permeate the wound before suturing. The specimens were harvested at 6 weeks after injection and observed microscopically. FIGS. 15A and 15C show pictures of the femoral condyles 6 weeks post injection with either a mixture of hChon and hChon-TGF-β1 cells (A) or hChon alone (C). FIGS. 15B and 15D show Mason's trichrome staining of sections from the femoral condyle injected with either mixture of hChon and hChon-TGF-β1 cells (B) or hChon alone (D). [Original magnification: (B & D)×12.5].

Example XIV

Regeneration of Cartilage with Injection of Mixture of Rabbit Buffy Coat and NIH3T3-TGF-β1 Cells in Rabbits with a Partial Cartilage Defect—New Zealand white rabbits weighing 2.0-2.5 kg were selected for the animal study. These rabbits were mature and had a tidemark. The knee joint was exposed and a partial cartilage defect (3 mm×6 mm, 1-2 mm deep) was made on the hyaline cartilage layer of the femoral condyle with a surgical knife. Either control rabbit buffy coat (rBC), or mixture of rabbit buffy coat and TGF-β1-producing cells (NIH3T3-TGF-β1, 15-20 μl of 2×10$^6$ cells/ml) was loaded into the defect and then left in the defect for 15-20 min to allow the mixture to permeate the wound before suturing. The femoral condyles were harvested at 6 or 8 weeks post injection.

The specimens were harvested at 6 or 8 weeks after loading and examined histologically. FIGS. 16A, C, and E show pictures of the femoral condyles 6 or 8 weeks post loading with either the mixture of rBC and NIH3T3-TGF-β1 cells (A and C) or buffy coat alone (E). FIGS. 16 B, D, and F show Mason's trichrome staining of sections from the femoral condyle loaded with the mixture of rBC and NIH3T3-TGF-β1 cells (B & D) or rBC alone (F). [Original magnification: (B, D, & F)×12.5].

Regeneration of hyaline cartilage was obtained in rabbits injected with a mixture of rabbit buffy coat and NIH3T3-TGF-β1 cells at 6 or 8 weeks after injection. In contrast, no significant regeneration of hyaline cartilage was found when rabbit buffy coat alone was injected at 8 weeks after injection.

Example XV

Regeneration Of Cartilage With Mixed-Cell (Human Chondrocytes And Human Chondrocyte-TGF-β1 Cells) Injection with Greenplast (GP) In Rabbits With A Partial or Full-Thickness Defect—A mixture of hChon and hChon-TGF-β1 cells was injected into the rabbit knee joint containing a partial or full-thickness cartilage defect (3 mm×5 mm, 1-2 mm or 2-3 mm deep) on the femoral condyle. The cell mixture (10-15 μl or 20-25 μl of $2\times10^6$ cells/ml, 1:1 ratio of hChon and hChon-TGF-β1 with 1:100 diluted GP) was loaded to the top of the defect and then left in the defect for 15-20 min to allow the cells to permeate the wound before suturing. The specimens were harvested at 6 weeks after injection and observed microscopically. FIGS. 17A and 17C show pictures of the femoral condyles 6 weeks post injection with a mixture of hChon and hChon-TGF-β1 cells at either a partial (A) or full-thickness defect (C). FIGS. 17B and 17D show Mason's trichrome staining of sections from the femoral condyle injected with a mixture of hChon and hChon-TGF-β1 cells at a partial (B) or full-thickness defect (D). [Original magnification: (B& D)×12.5].

All of the references cited herein are incorporated by reference in their entirety.

Whereas particular embodiments of this invention have been described above for purposes of illustration, it will be evident to those persons skilled in the art that numerous variations of the details of the present invention may be made without departing from the invention as defined in the appended claims.

What is claimed is:

1. A composition comprising a treatment effective amount of a population of somatic fibroblast or chondrocyte cells transfected or transduced with a therapeutic gene, and an adhesive effective amount of buffy coat for administration into a joint space in a mammal in need thereof, wherein said cells and buffy coat material are autologous, syngeneic, or are allogeneic with respect to each other.

2. The composition according to claim 1, wherein said gene encodes a cytokine.

3. The composition according to claim 2, wherein said cytokine belongs to TGF-β superfamily.

4. The composition according to claim 3, wherein said cytokine is TGF-β1, TGF-β2, TGF-β3, BMP-2, BMP-3, BMP-4, BMP-5, BMP-6, BMP-7, or BMP-9.

5. The composition according to claim 4, wherein said gene is TGF-β1 or BMP-2.

6. The composition according to claim 1, wherein said cells are irradiated.

7. The composition according to claim 1, wherein said cells are mixed with cells that are not transfected or transduced with any DNA.

8. A storage container for storing cells at a temperature of about −70° C. to about −196° C., comprising the composition according to claim 1.

9. A method of localizing gene expression at a joint space in a mammal, comprising mixing an adhesive effective amount of buffy coat with therapeutic somatic fibroblast or chondrocyte cells to form a composition, wherein said cells are autologous, syngeneic, or allogeneic with respect to said mammal, and administering the composition to the site in need thereof.

10. The method according to claim 9, wherein said somatic cells are transfected or transduced with a recombinant vector comprising a therapeutic gene.

11. The method according to claim 10, wherein said therapeutic gene is transforming growth factor β (TGF-β) or bone morphogenetic protein (BMP).

12. The method according to claim 11, wherein said gene is TGF-β1, TGF-β2, TGF-β3, BMP-2, BMP-3, BMP-4, BMP-5, BMP-6, or BMP-7.

13. The method according to claim 12, wherein said gene is TGF-β1 or BMP -2.

14. The method according to claim 9, wherein said cells are irradiated.

15. The method according to claim 9, wherein the cells are syngeneic with respect to the host recipient.

16. The method according to claim 9, wherein said somatic cells comprise a mixture of a first type of cells that are transfected or transduced with DNA encoding a therapeutic gene, and a second type of cells that are not transfected or transduced with DNA encoding a therapeutic gene.

17. The method of claim 9, wherein said cells are stored prior to transplantation.

18. The method of claim 17, wherein said cells are stored in a cryopreservative prior to transplantation.

19. The method of claim 10, wherein said transfection or transduction is accomplished by liposome encapsulation, calcium phosphate coprecipitation, electroporation, DEAE—dextran mediation or viral mediation.

20. A method of generating hyaline cartilage in a mammal comprising:
injecting a composition according to claim 3
into a joint space of a mammal such that expression of the cytokine within the joint space generates hyaline cartilage in the joint space.

21. The method according to claim 20, wherein said cytokine is TGF-β1, TGF-β2, TGF-β3, BMP-2, BMP-3, BMP-4, BMP-5, BMP-6, BMP-7, or BMP-9.

22. The method according to claim 20, further comprising:
injecting, with said composition,a population of fibroblast or chondrocyte cells that have not been transfected or transduced with a gene encoding TGF-β or BMP.

23. The method according to claim 22, wherein said composition expresses a cytokine selected from TGF-β1, TGF-β2, TGF-β3, BMP-2, BMP-3, BMP-4, BMP-5, BMP-6, BMP-7, or BMP-9.

24. A method of treating osteoarthritis comprising:
injecting a composition according to claim 3
into a joint space of a mammal such that expression of the cytokine within the joint space generates bone and cartilage in the joint space.

25. The method according to claim 24, wherein said cytokine is TGF-β1, TGF-β2, TGF-β3, BMP-2, BMP-3, BMP-4, BMP-5, BMP-6, BMP-7, or BMP-9.

26. The method according to claim 24, further comprising:
injecting, with said composition, a population of fibroblast or chondrocyte cells that have not been transfected or transduced with a gene encoding TGF-β or BMP.

27. The method according to claim 26, wherein said composition expresses a cytokine selected from TGF-β1, TGF-β2, TGF-β3, BMP-2, BMP-3,BMP-4, BMP-5, BMP-6, BMP-7, or BMP-9.

* * * * *